United States Patent
Fukase et al.

(10) Patent No.: US 12,215,090 B2
(45) Date of Patent: Feb. 4, 2025

(54) AGENTS AND METHODS FOR TREATING DYSPROLIFERATIVE DISEASES

(71) Applicant: Memorial Sloan-kettering Cancer Center, New York, NY (US)

(72) Inventors: Yoshiyuki Fukase, Edgewater, NJ (US); Mark Duggan, Teuesta, FL (US); Hans-Guido Wendel, New York, NY (US); Kamini Singh, New York, NY (US)

(73) Assignees: Memorial Sloan Kettering Cancer Center, New York, NY (US); Tri-Institutional Therapeutics Discovery Institute, Inc., New York, NY (US)

( * ) Notice: Subject to any disclaimer, the term of this patent is extended or adjusted under 35 U.S.C. 154(b) by 619 days.

(21) Appl. No.: 16/970,918

(22) PCT Filed: Feb. 18, 2019

(86) PCT No.: PCT/US2019/018441
§ 371 (c)(1),
(2) Date: Aug. 18, 2020

(87) PCT Pub. No.: WO2019/161345
PCT Pub. Date: Aug. 22, 2019

(65) Prior Publication Data
US 2020/0392099 A1 Dec. 17, 2020

Related U.S. Application Data

(60) Provisional application No. 62/632,372, filed on Feb. 19, 2018.

(51) Int. Cl.
*C07D 307/93* (2006.01)
*A61K 31/343* (2006.01)
*A61P 35/00* (2006.01)

(52) U.S. Cl.
CPC ............ *C07D 307/93* (2013.01); *A61P 35/00* (2018.01)

(58) Field of Classification Search
CPC .... C07D 307/93; A61P 35/00; C07F 9/65517; A61K 31/343
See application file for complete search history.

(56) References Cited

U.S. PATENT DOCUMENTS

| | | |
|---|---|---|
| 6,710,075 B2 | 3/2004 | Meurer-Grimes et al. |
| 7,816,544 B2 | 10/2010 | Jones, II et al. |
| 8,030,347 B2 | 10/2011 | Diedrichs et al. |
| 8,137,509 B2 | 3/2012 | Porco, Jr. et al. |
| 8,404,088 B2 | 3/2013 | Porco, Jr. et al. |
| 2008/0177093 A1 | 7/2008 | Jones, II et al. |
| 2009/0299081 A1 | 12/2009 | Porco, Jr. et al. |
| 2010/0168084 A1 | 7/2010 | Huber et al. |
| 2012/0101153 A1 | 4/2012 | Desaubry et al. |
| 2012/0238766 A1 | 9/2012 | Porco, Jr. et al. |
| 2015/0087598 A1 | 3/2015 | Kufe |
| 2015/0219624 A1 | 8/2015 | Wendel et al. |
| 2017/0096723 A1 | 4/2017 | Kasuya et al. |
| 2017/0137400 A1 | 5/2017 | Marion et al. |
| 2017/0145026 A1 | 5/2017 | Ernst et al. |
| 2017/0348422 A1 | 12/2017 | Pillow et al. |
| 2018/0086729 A1 | 3/2018 | Marion et al. |

FOREIGN PATENT DOCUMENTS

| | | |
|---|---|---|
| DE | 19934952 | 3/2000 |
| EP | 08169536.3 | 5/2010 |
| WO | WO 2005092876 | 10/2005 |
| WO | WO 2006007634 | 1/2006 |
| WO | WO 2007139749 | 12/2007 |
| WO | WO 2010057981 | 5/2010 |
| WO | WO2010060891 | 6/2010 |
| WO | WO 2011140334 | 10/2011 |
| WO | WO 2013016658 | 1/2013 |
| WO | WO 2013170257 | 11/2013 |
| WO | WO 2015085221 | 6/2015 |
| WO | WO2017091585 | 6/2017 |

OTHER PUBLICATIONS

RN1352914-59-0, registry database compound, entry date 2012.*
RN1352914-53-4, registry database compound, entry date 2012.*
RN256497-39-9, registry database compound, entry date 2000.*
Rodrigo et al., J. Med. Chem., 2012, 55(1), 558-562.*
Cancer-Prevention, 2023, https://www.cancerresearchuk.org/about-cancer/causes-of-cancer/can-cancer-be-prevented-0.*
International Search Report of corresponding PCT Application No. PCT/US2019/018441 dated Jul. 26, 2019.
PCT/US19/18441 International Search Report dated Jun. 26, 2019.
European Search Report from EP 19753769.9 dated Jul. 5, 2021.
Office action from IL 276639 dated Augsut 3, 2022.
Office action for IN202017040549 dated Jan. 13, 2022.
Adams et al., Total Synthesis of the Potent Anticancer Aglaia Metabolites (−)-Silvestrol and (−)-Episilvestrol and the Active Analogue(−)-4'-Desmethoxyepisilvestrol, J. Am. Chem. Soc. 2009, 131, 1607-1616.
Aubert et al., Acta Cryst. (2013). E69, o52-o53.
Barjau et al., Installation of Amine Moieties into a Polycyclic Anodic Product Derived from 2,4-Dimethylphenol, Chem. Eur. J. 2011, 17, 14785-14791.

(Continued)

*Primary Examiner* — Sun Jae Yoo
(74) *Attorney, Agent, or Firm* — Mark S. Cohen; PEARL COHEN ZEDEK LATZNER BARATZ LLP

(57) ABSTRACT

Compounds are described with the general formula (I) wherein $R_1$, $R_2$, $R_3$, $R_4$, $R_5$, $R_6$, $R_7$, $R_8$, $R_9$, $R_{10}$, $R_{11}$, $R_{12}$, and n are defined as anywhere herein, which are useful for the treatment of cancer and other dysproliferative diseases.

31 Claims, 6 Drawing Sheets

Specification includes a Sequence Listing.

(56) References Cited

OTHER PUBLICATIONS

Cai et al., Progress in the Total Synthesis of Rocaglamide, ISRN Organic Chemistry, vol. 2011, Article ID 239817, 7 pages.

Chambers et al. Total Synthesis of 2′″,5′″-Diepisilvestrol and Its C1′″ Epimer: Key Structure Activity Relationships at C1′″ and C2′″, J. Nat. Prod. 2012, 75, 1500-1504.

Chu et al., Translation Inhibition by Rocaglates is Independent of eIF4E Phosphorylation Status, Molecular Cancer Therapeutics (2016), 15(1), 136-141.

Dobler et al., Total synthesis of (±)-rocaglamide and some aryl analogues, Tetrahedron Letters 42 (2001) 8281-8284.

El Sous et al., Total Synthesis of (−)-Episilvestrol and (−)-Silvestrol, Angew. Chem. Int. Ed. 2007, 46, 7835-7838.

Engler et al., Stereospecific Lewis Acid-Promoted Reactions of Styrenyl Systems with 2-Alkoxy-(6-alkyl)-1,4-benzoquinone: Scope, Limitations, and Synthetic Applications, J. Org. Chem. 1994,59, 6567-6587.

Gerard et al., Enantioselective Photocycloaddition Mediated by Chiral Brønsted Acids: Asymmetric Synthesis of the Rocaglamides, J. Am. Chem. Soc. 2006, 128, 7754-7755.

Gerard et al., Enantioselective Synthesis of the Complex Rocaglate (−)-Silvestrol, Angew. Chem. Int. Ed. 2007, 46, 7831-7834.

Hawkins et al., Simplified Silvestrol Analogues with Potent Cytotoxic Activity, (2014), 9(7), 1556-1566.

Hwang et al., Silvestrol and Episilvestrol, Potential Anticancer Rocaglate Derivatives from Aglaia silvestris, J. Org. Chem. 2004, 69, 3350-3358.

Jin et al., Targeting The eIF4A RNA Helicase Blocks Translation of the MUC1-C Oncoprotein, Oncogene (2013), 32(17), 2179-2188; Published in final edited form as: Oncogene. Apr. 25, 2013; 32(17): 2179-2188, Published online Nov. 19, 2015.

Jin et al., 2010, Isolation and Characterization of Minor Analogues of Silvestrol and other Constituents from a Large-scale Recollection of Aglaia foveolate, J Nat Prod 2010; 73(11):1873-1878.

Kinghorn et al., The Relevance of Higher Plants in Lead Compound Discovery Programs, J. Nat. Prod. 2011, 74, 1539-1555.

Liu et al, Synthetic Silvestrol Analogues as Potent and Selective Protein Synthesis Inhibitors, J. Med. Chem. 2012, 55, 8859-8878.

Malona et al., Total Synthesis of (±)-Rocaglamide via Oxidation-Initiated Nazarov Cyclization, J. Org. Chem. 2012, 77, 1891-1908.

Pan et al., 2014, Rocaglamide, silvestrol and structurally related bioactive compounds from *Aglaia* species. Nat. Prod. Rep. 31(7): 924-939.

Pan et al., Bioactive Flavaglines and Other Constituents Isolated from Aglaia perviridis, J. Nat. Prod. 2013, 76, 394-404.

Pan et al., Isolation and Characterization of Minor Analogues of Silvestrol and other Constituents from a Large-scale Recollection of Aglaia foveolate, J Nat Prod (2010) 73: 1873-1878.

Polier et al., The Natural Anticancer Compounds Rocaglamides Inhibit the Raf-MEK-ERK Pathway by Targeting Prohibitin 1 and 2, Chemistry & Biology 19: 1093-1104, 2012.

Ribiero et al., Recent advances in the biology and chemistry of the flavaglines, Bioorganic & Medicinal Chemistry 20 (2012) 1857-1864.

Roche et al., Biomimetic Photocycloaddition of 3-Hydroxyflavones: Synthesis and Evaluation of Rocaglate Derivatives as Inhibitors of Eukaryotic Translation, Angew. Chem. Int. Ed. 2010, 49, 6533-653.

Rodrigo et al., Synthesis of Rocaglamide Hydroxamates and Related Compounds as Eukaryotic Translation Inhibitors: Synthetic and Biological Studies, Med Chem. Jan. 12, 2012; 55(1):558-562.

Sadlish et al., Evidence for a functionally relevant rocaglamide binding site on the eIF4A-RNA complex, ACS Chem Biol 2013; 8:1519-1527.

\* cited by examiner

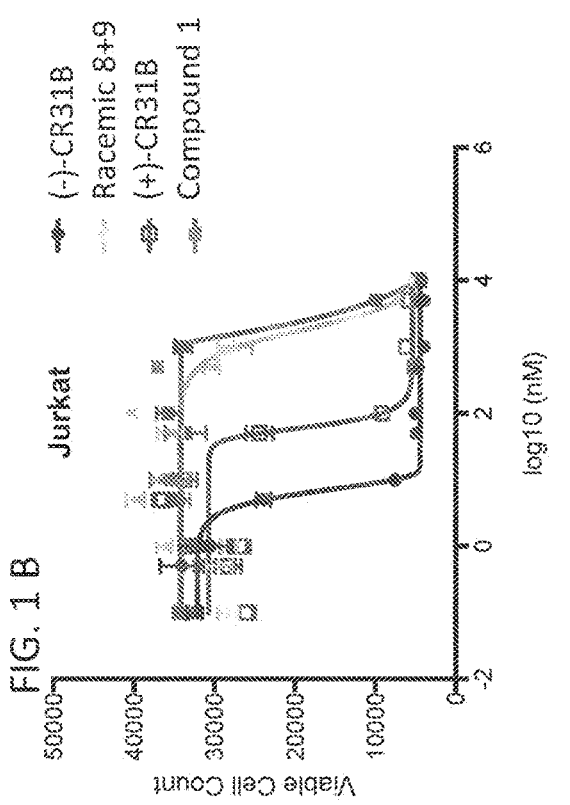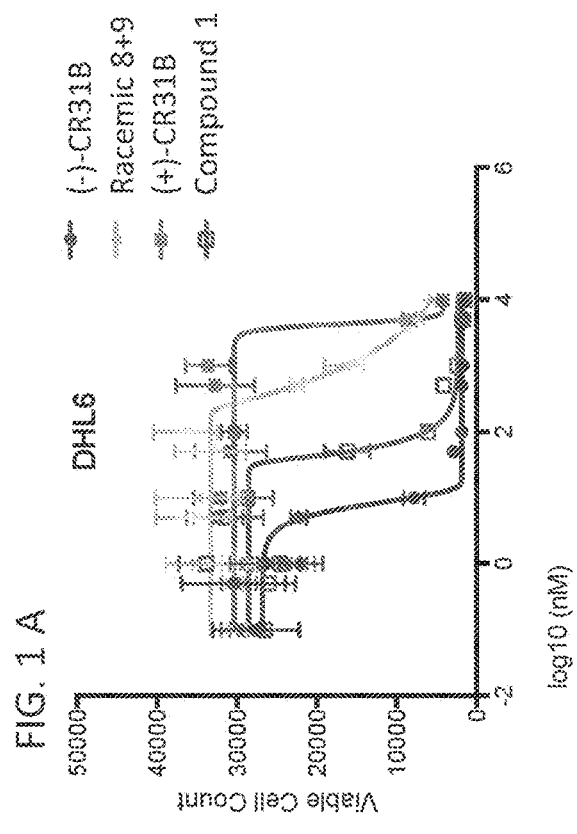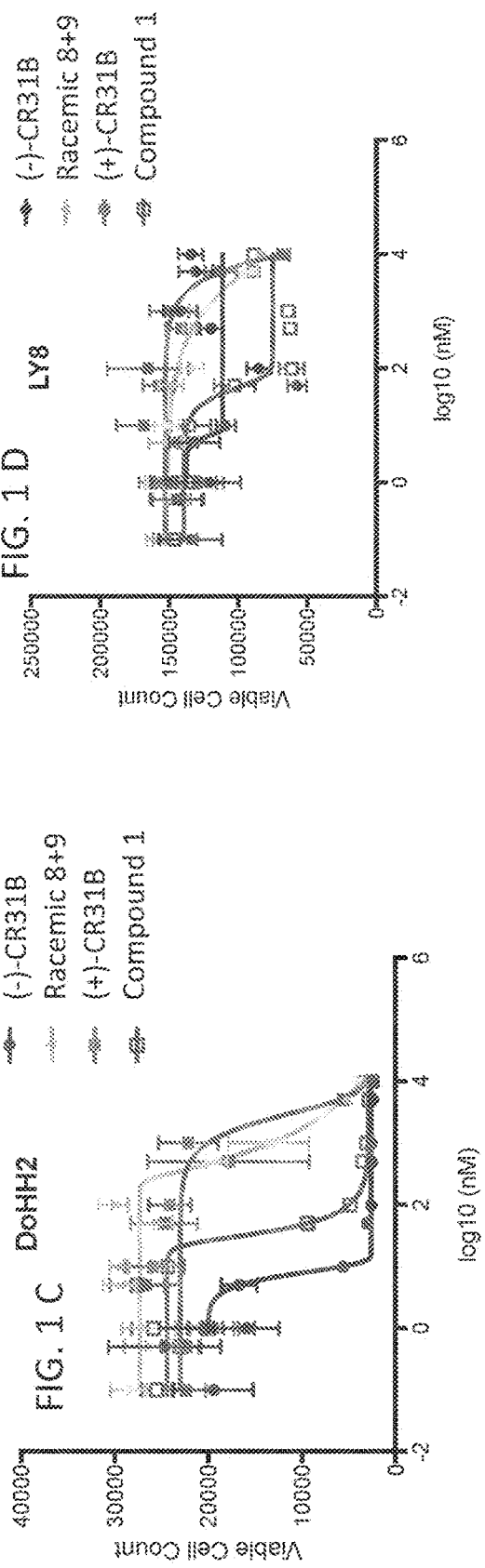

AGENTS AND METHODS FOR TREATING DYSPROLIFERATIVE DISEASES

CROSS-REFERENCE TO RELATED APPLICATIONS

This application is a National Phase Application of PCT International Application No. PCT/US2019/018441, International Filing Date Feb. 18, 2019, claiming the benefit of U.S. Patent Application(s) No(s). 62/632,372, filed Feb. 19, 2020, which are hereby incorporated by reference.

GOVERNMENT INTEREST STATEMENT

This invention was made with government support under CA207217 awarded by the National Institutes of Health. The government has certain rights in the invention.

REFERENCE TO SEQUENCE LISTING

The present application includes a Sequence Listing in electronic format. The Sequence Listing is provided as a file entitled "P-574266-US_SQL_ST25_080CT24.txt", created on Oct. 8, 2024, which is 835 bytes in size. The information in the electronic format of the Sequence Listing is incorporated herein by reference in its entirety.

FIELD OF THE INVENTION

The invention relates to novel compounds and uses thereof for the treatment of cancer and other dysproliferative diseases.

BACKGROUND OF THE INVENTION

The activation of protein translation contributes to malignant transformation. For example, activation of the RAS, ERK, and AKT signaling pathways stimulates cap-dependent translation. Moreover, the rate limiting eIF4E translation factor is expressed at high levels in many cancers and can transform rodent fibroblasts and promote tumor development in vivo. Accordingly, cap-dependent translation is an emerging target for cancer therapies. Notably, three distinct natural compounds target the eIF4A helicase and these are the rocaglate silvestrol isolated from plants in the Malaysian rainforest, the macrolide pateamine A found in marine sponges off the coast of New Zealand, and the steroid hippuristanol which is produced by pacific corals. These compounds show promising preclinical activity against different cancers. Other strategies to inhibit translation include rapamycin and mTORC1 kinase inhibitors, inhibitors of the eIF4E kinase MNK1/2, a peptide (4EGI-1) that interferes with the eIF4E -eIF4G interaction, and the anti-viral ribavirin that may bind eIF4E directly.

Rocaglates are members of a super family of natural products incorporating a common cyclopentyl[b]furan core. Many members of this family, including the most extensively investigated analog silvestrol, are potent inhibitors of translation initiation and exhibit single-agent, antineoplastic activity in preclinical assays (both in vitro and in vivo). A significant body of evidence suggests that these agents are inhibitors of eIF4A RNA helicase. They function by preventing translation initiation by hindering helicase unwinding via eIF4A inhibition and interfering with ribosome recruitment to mRNA templates. Briefly, eIF4A is selectively required for the translation of mRNAs with G-quadruplex (GQ) structures in their 5′UTRs. These–220 GQ mRNAs include oncogenes such as c-MYC, N-Myc, L-Myc, N-RAS, MYB, Notch1, BCL2, and CDK6.

It is toward the identification of additional inhibitors of protein translation useful in the treatment of cancers and other dysproliferative diseases that the present invention is directed.

SUMMARY OF THE INVENTION

The present invention provides a compound represented by formula (I)

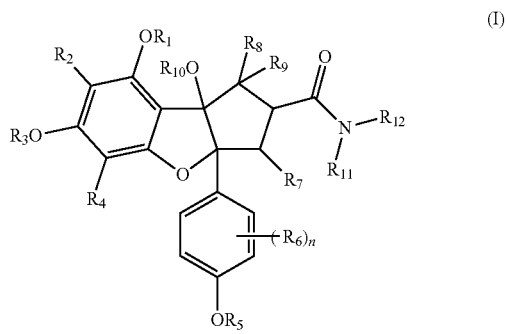

wherein $R_1$, $R_3$, and $R_5$ are each independently H, alkyl, —P(O)(OH)(OH), —$CH_2$—P(O)(OH)(OH), —P(O)(OH)(O-alkyl), —$CH_2$—P(O)(OH)(O-alkyl), —P(O)(O-alkyl)(O-alkyl), —$CH_2$—P(O)(O-alkyl)(O-alkyl), or (CO)-alkyl, or a pharmaceutically acceptable salt of —P(O)(OH)(OH), —$CH_2$—P(O)(OH)(OH), —P(O)(OH)(O-alkyl), or —$CH_2$—P(O)(OH)(O-alkyl), wherein at least one of $R_1$, $R_3$, and $R_5$ is H, —P(O)(OH)(OH), —$CH_2$—P(O)(OH)(OH), —P(O)(OH)(O-alkyl), —$CH_2$—P(O)(OH)(O-alkyl), —P(O)(O-alkyl)(O-alkyl), —$CH_2$—P(O)(O-alkyl)(O-alkyl), or a pharmaceutically acceptable salt of —P(O)(OH)(OH), —$CH_2$—P(O)(OH)(OH), —P(O)(OH)(O-alkyl), or —$CH_2$—P(O)(OH)(O-alkyl);

$R_2$ and $R_4$ are each independently H, alkyl, halo, nitro, OH, O-alkyl, SH, S-alkyl, CN, haloalkyl, O-haloalkyl, $NR_aR_b$, (CO)-alkyl, (CO)OH, (CO)O-alkyl, $SO_2NR_aR_b$, (CO)$NR_aR_b$, NH(CO)-alkyl, cycloalkyl, heterocycloalkyl, aryl, or heteroaryl, wherein aryl and heteroaryl are optionally substituted with alkyl, halo, nitro, OH, O-alkyl, SH, S-alkyl, CN, haloalkyl, O-haloalkyl, and $NR_aR_b$;

$R_6$ is alkyl, halo, nitro, OH, O-alkyl, SH, S-alkyl, CN, haloalkyl, O-haloalkyl, $NR_aR_b$, (CO)-alkyl, (CO)OH, (CO)O-alkyl, $SO_2NR_aR_b$, (CO)$NR_aR_b$, NH(CO)-alkyl, cycloalkyl, heterocycloalkyl, aryl, or heteroaryl, wherein aryl and heteroaryl are optionally substituted with alkyl, halo, nitro, OH, O-alkyl, SH, S-alkyl, CN, haloalkyl, O-haloalkyl, and $NR_aR_b$;

$R_7$ is aryl or heteroaryl, wherein aryl and heteroaryl are optionally substituted with alkyl, halo, nitro, OH, O-alkyl, SH, S-alkyl, CN, haloalkyl, O-haloalkyl, and $NR_aR_b$;

$R_8$ and $R_9$ are each independently H, OH, alkyl, halo, O-alkyl, SH, S-alkyl, CN, haloalkyl, O-haloalkyl, $NR_aR_b$, (CO)OH, (CO)O-alkyl, $SO_2NR_aR_b$, (CO)$NR_aR_b$, or NH(CO)-alkyl;

$R_{10}$ is H, alkyl, (CO)-alkyl, or (CO)$NR_aR_b$;

$R_{11}$ and $R_{12}$ are each independently H, OH, alkyloxy, cycloalkyloxy, heterocycloalkyloxy, cycloalkylalkyloxy, heterocycloalkylalkyloxy, arylalkyloxy, heteroarylalkyloxy, aryloxy, or heteroaryloxy;

$R_a$ and $R_b$ are each H or alkyl, or $R_a$ and $R_b$, together with the nitrogen atom they are attached, form a heterocycloalkyl group; and n is an integer from 0 to 4, or a pharmaceutically acceptable salt thereof.

The present invention further provides a pharmaceutical composition comprising a compound of the invention as described herein, or a pharmaceutically acceptable salt thereof, and a pharmaceutically-acceptable carrier.

The present invention further provides a method for preventing, treating or intervening in the recurrence of a cancer or dysproliferative disease in a subject comprising administering to the subject a compound of the invention as described herein, or a pharmaceutically acceptable salt thereof, or a pharmaceutical composition thereof.

The present invention further provides a method for preventing, treating or intervening in the recurrence of fibrosis or a fibroproliferative disease in a subject comprising administering to the subject a compound of the invention as described herein, or a pharmaceutically acceptable salt thereof, or a pharmaceutical composition thereof.

The details of one or more embodiments of the invention are set forth in the accompa-nying the description below. Other features, objects, and advantages of the invention will be apparent from the description and drawings, and from the claims.

BRIEF DESCRIPTION OF THE FIGURES

FIGS. 1A, 1B, 1C, and 1D show the effect of compounds of the invention on viability of lymphoma and leukemia cells in vitro.

DETAILED DESCRIPTION OF THE INVENTION

Figure 2:
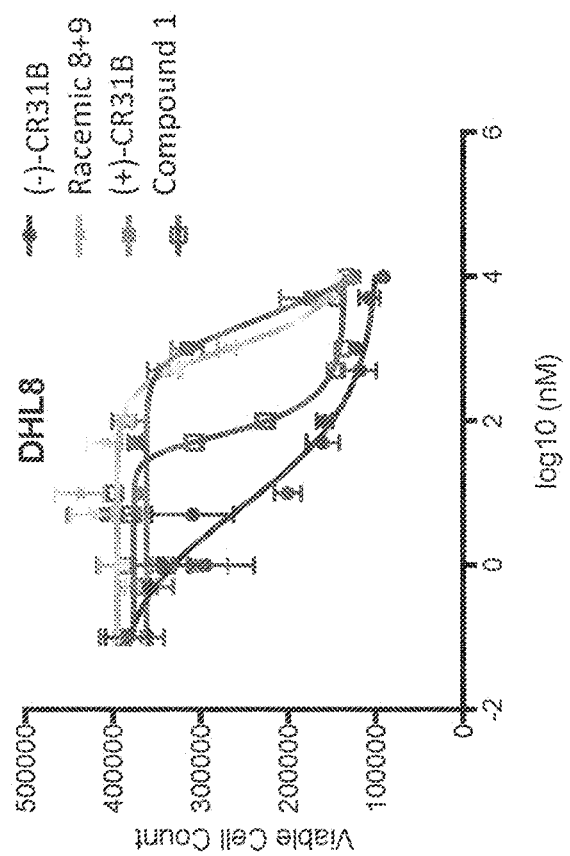
FIG. 2 shows the effect of compounds of the invention on viability of DHL8 lymphoma cells in vitro.

The present invention provides a compound represented by formula (I)

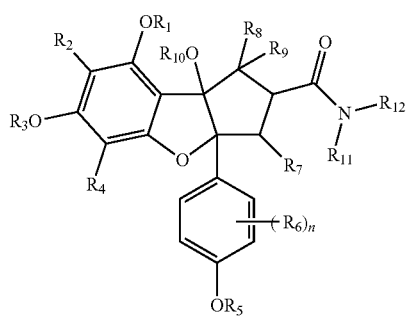

wherein $R_1$, $R_3$, and $R_5$ are each independently H, alkyl, —P(O)(OH)(OH), —CH$_2$—P(O)(OH)(OH), —P(O)(OH)(O-alkyl), —CH$_2$—P(O)(OH)(O-alkyl), —P(O)(O-alkyl)(O-alkyl), —CH$_2$—P(O)(O-alkyl)(O-alkyl), or (CO)-alkyl, or a pharmaceutically acceptable salt of —P(O)(OH)(OH), —CH$_2$—P(O)(OH)(OH), —P(O)(OH)(O-alkyl), or —CH$_2$—P(O)(OH)(O-alkyl), wherein at least one of $R_1$, $R_3$, and $R_5$ is H, —P(O)(OH)(OH), —CH$_2$—P(O)(OH)(OH), —P(O)(OH)(O-alkyl), —CH$_2$—P(O)(OH)(O-alkyl), —P(O)(O-alkyl)(O-alkyl), —CH$_2$—P(O)(O-alkyl)(O-alkyl), or a pharmaceutically acceptable salt of —P(O)(OH)(OH), —CH$_2$—P(O)(OH)(OH), —P(O)(OH)(O-alkyl), or —CH$_2$—P(O)(OH)(O-alkyl);

$R_2$ and $R_4$ are each independently H, alkyl, halo, nitro, OH, O-alkyl, SH, S-alkyl, CN, haloalkyl, O-haloalkyl, NR$_a$R$_b$, (CO)-alkyl, (CO)OH, (CO)O-alkyl, SO$_2$NR$_a$R$_b$, (CO)NR$_a$R$_b$, NH(CO)-alkyl, cycloalkyl, heterocycloalkyl, aryl, or heteroaryl, wherein aryl and heteroaryl are optionally substituted with alkyl, halo, nitro, OH, O-alkyl, SH, S-alkyl, CN, haloalkyl, O-haloalkyl, and NR$_a$R$_b$;

$R_6$ is alkyl, halo, nitro, OH, O-alkyl, SH, S-alkyl, CN, haloalkyl, O-haloalkyl, NR$_a$R$_b$, (CO)-alkyl, (CO)OH, (CO)O-alkyl, SO$_2$NR$_a$R$_b$, (CO)NR$_a$R$_b$, NH(CO)-alkyl, cycloalkyl, heterocycloalkyl, aryl, or heteroaryl, wherein aryl and heteroaryl are optionally substituted with alkyl, halo, nitro, OH, O-alkyl, SH, S-alkyl, CN, haloalkyl, O-haloalkyl, and NR$_a$R$_b$;

$R_7$ is aryl or heteroaryl, wherein aryl and heteroaryl are optionally substituted with alkyl, halo, nitro, OH, O-alkyl, SH, S-alkyl, CN, haloalkyl, O-haloalkyl, and NR$_a$R$_b$;

$R_8$ and $R_9$ are each independently H, OH, alkyl, halo, O-alkyl, SH, S-alkyl, CN, haloalkyl, O-haloalkyl, NR$_a$R$_b$, (CO)OH, (CO)O-alkyl, SO$_2$NR$_a$R$_b$, (CO)NR$_a$R$_b$, or NH(CO)-alkyl;

$R_{10}$ is H, alkyl, (CO)-alkyl, or (CO)NR$_a$R$_b$;

$R_{11}$ and $R_{12}$ are each independently H, OH, alkyloxy, cycloalkyloxy, heterocycloalkyloxy, cycloalkylalkyloxy, heterocycloalkylalkyloxy, arylalkyloxy, heteroarylalkyloxy, aryloxy, or heteroaryloxy;

$R_a$ and $R_b$ are each H or alkyl, or $R_a$ and $R_b$, together with the nitrogen atom they are attached, form a heterocycloalkyl group; and n is an integer from 0 to 4, or a pharmaceutically acceptable salt thereof.

In some embodiments, $R_1$1 is H. In some embodiments, $R_{11}$ and $R_{12}$ both are H. In some embodiments, $R_{12}$ is alkyloxy or cycloalkyloxy. In some embodiments, $R_{12}$ is alkyloxy. In certain embodiments, $R_{12}$ is OMe. In some embodiments, $R_{11}$ is H and $R_{12}$ is alkyloxy or cycloalkyloxy. In other embodiments, $R_1$l is H and $R_{12}$ is OMe.

In some embodiments, $R_3$ is H, —P(O)(OH)(OH), —CH$_2$—P(O)(OH)(OH), —P(O)(OH)(O-alkyl), —CH$_2$—P(O)(OH)(O-alkyl), —P(O)(O-alkyl)(O-alkyl), —CH$_2$—P(O)(O-alkyl)(O-alkyl), or a pharmaceutically acceptable salt of —P(O)(OH)(OH), —CH$_2$—P(O)(OH)(OH), —P(O)(OH)(O-alkyl), or —CH$_2$—P(O)(OH)(O-alkyl). In some embodiments, $R_3$ is H. In other embodiments, $R_3$ is —P(O)(OH)(OH), —CH$_2$—P(O)(OH)(OH), —P(O)(OH)(O-alkyl), —CH$_2$—P(O)(OH)(O-alkyl), —P(O)(O-alkyl)(O-alkyl), —CH$_2$—P(O)(O-alkyl)(O-alkyl), or a pharmaceutically acceptable salt of —P(O)(OH)(OH), —CH$_2$—P(O)(OH)(OH), —P(O)(OH)(O-alkyl), or —CH$_2$—P(O)(OH)(O-alkyl). In other embodiments, $R_3$ is —P(O)(OH)(OH), —P(O)(OH)(O-alkyl), or —P(O)(O-alkyl)(O-alkyl), or a pharmaceutically acceptable salt of —P(O)(OH)(OH) or —P(O)(OH)(O-alkyl). In some embodiments, $R_3$ is —P(O)(OH)(OH) or —CH$_2$—P(O)(OH)(OH), or a pharmaceutically acceptable salt thereof. In some embodiments, $R_3$ is —P(O)(ONa)(OH). In other embodiments, $R_3$ is —P(O)(ONa)(ONa). In certain embodiments, $R_3$ is —P(O)(ONa)(O-alkyl).

In some embodiments, $R_5$ is H, —P(O)(OH)(OH), —CH$_2$—P(O)(OH)(OH), —P(O)(OH)(O-alkyl), —CH$_2$—P(O)(OH)(O-alkyl), —P(O)(O-alkyl)(O-alkyl), —CH$_2$—P(O)(O-alkyl)(O-alkyl), or a pharmaceutically acceptable salt of —P(O)(OH)(OH), —CH$_2$—P(O)(OH)(OH), —P(O)(OH)(O-alkyl), or —CH$_2$—P(O)(OH)(O-alkyl). In some embodiments, $R_5$ is H. In other embodiments, $R_5$ is —P(O)(OH)(OH), —CH$_2$—P(O)(OH)(OH), —P(O)(OH)(O-alkyl), —CH$_2$—P(O)(OH)(O-alkyl), —P(O)(O-alkyl)(O-alkyl), —CH$_2$—P(O)(O-alkyl)(O-alkyl), or a pharmaceutically acceptable salt of —P(O)(OH)(OH), —CH$_2$—P(O)(OH)(OH), —P(O)(OH)(O-alkyl), or —CH$_2$—P(O)(OH)(O-alkyl). In other embodiments, $R_5$ is —P(O)(OH)(OH), —P(O)(OH)(O-alkyl), or —P(O)(O-alkyl)(O-alkyl), or a pharmaceutically acceptable salt of —P(O)(OH)(OH) or —P(O)(OH)(O-alkyl). In some embodiments, $R_5$ is —P(O)(OH)(OH) or —CH$_2$—P(O)(OH)(OH), or a pharmaceutically acceptable salt thereof. In some embodiments, $R_5$ is —P(O)(ONa)(OH). In other embodiments, $R_5$ is —P(O)(ONa)(ONa). In certain embodiments, $R_5$ is —P(O)(ONa)(O-alkyl).

In some embodiments, $R_1$ is H, —P(O)(OH)(OH), —CH$_2$—P(O)(OH)(OH), —P(O)(OH)(O-alkyl), —CH$_2$—P(O)(OH)(O-alkyl), —P(O)(O-alkyl)(O-alkyl), —CH$_2$—P(O)(O-alkyl)(O-alkyl), or a pharmaceutically acceptable salt of —P(O)(OH)(OH), —CH$_2$—P(O)(OH)(OH), —P(O)(OH)(O-alkyl), or —CH$_2$—P(O)(OH)(O-alkyl). In some embodiments, $R_1$ is H. In other embodiments, $R_1$ is —P(O)(OH)(OH), —CH$_2$—P(O)(OH)(OH), —P(O)(OH)(O-alkyl), —CH$_2$—P(O)(OH)(O-alkyl), —P(O)(O-alkyl)(O-alkyl), —CH$_2$—P(O)(O-alkyl)(O-alkyl), or a pharmaceutically acceptable salt of —P(O)(OH)(OH), —CH$_2$—P(O)(OH)(OH), —P(O)(OH)(O-alkyl), or —CH$_2$—P(O)(OH)(O-alkyl). In other embodiments, $R_1$ is —P(O)(OH)(OH), —P(O)(OH)(O-alkyl), or —P(O)(O-alkyl)(O-alkyl), or a pharmaceutically acceptable salt of —P(O)(OH)(OH) or —P(O)(OH)(O-alkyl). In some embodiments, $R_1$ is —P(O)(OH)(OH) or —CH$_2$—P(O)(OH)(OH), or a pharmaceutically acceptable salt thereof. In some embodiments, $R_1$ is —P(O)(OH)(OH). In some embodiments, the pharmaceutically acceptable salt of —P(O)(OH)(OH), —CH$_2$—P(O)(OH)(OH), —P(O)(OH)(O-alkyl), or —CH$_2$—P(O)(OH)(O-alkyl) is a sodium salt, a potassium salt, a calcium salt, or other salts known in the art. In some embodiments, $R_1$ is —P(O)(ONa)(OH). In other embodiments, $R_1$ is —P(O)(ONa)(ONa). In certain embodiments, $R_1$ is —P(O)(ONa)(O-alkyl). In some embodiments, $R_1$ is H. In other embodiments, $R_1$ is alkyl. In certain embodiments, $R_1$ is methyl.

In some embodiments, $R_2$ and $R_4$ are H. In some embodiments, n is 0. In other embodiments, n is 1. In some embodiments, n is 2, 3, or 4. In some embodiments, $R_2$ and $R_4$ are H and n is 0. In some embodiments, $R_{10}$ is H. In some embodiments, $R_8$ is H and $R_9$ is OH.

In some embodiments, the compound of formula (I) is represented by a compound of formula (II)

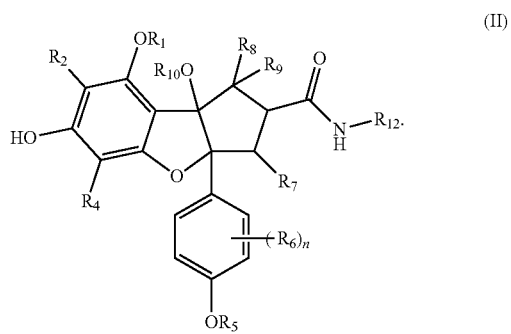

In some embodiments, in the compound of formula (II), $R_1$, $R_2$, $R_4$, $R_5$, $R_6$, $R_7$, $R_8$, $R_9$, $R_{10}$, $R_{12}$ and n are defined as anywhere herein. In some embodiments, $R_{12}$ is H or OMe. In some embodiments, $R_{12}$ is OMe. In other embodiments, $R_{12}$ is H.

In some embodiments, the compound of formula (I) is represented by a compound of formula (III)

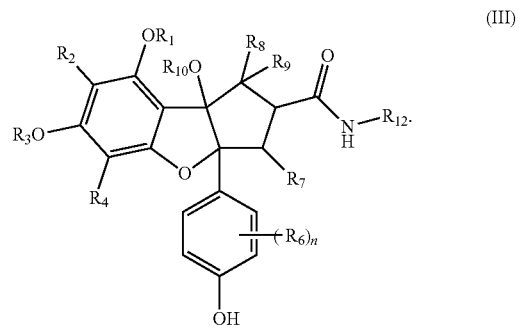

In some embodiments, in the compound of formula (III), $R_1$, $R_2$, $R_3$, $R_4$, $R_6$, $R_7$, $R_8$, $R_9$, $R_{10}$, $R_{12}$ and n are defined as anywhere herein. In some embodiments, $R_{12}$ is OMe. In other embodiments, $R_{12}$ is H.

In some embodiments, the compound of formula (I) is represented by a compound of formula (IV)

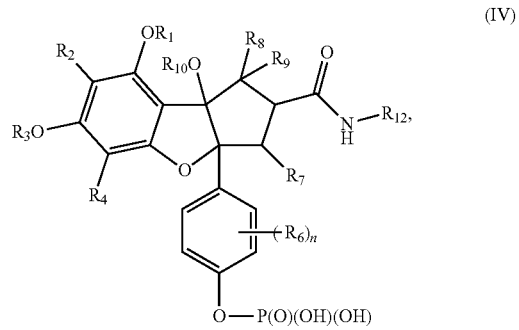

or a pharmaceutically acceptable salt thereof.

In some embodiments, in the compound of formula (IV), $R_1$, $R_2$, $R_3$, $R_4$, $R_6$, $R_7$, $R_8$, $R_9$, $R_{10}$, $R_{12}$ and n are defined as anywhere herein. In some embodiments, $R_{12}$ is alkyloxy or cycloalkyloxy. In some embodiments, $R_{12}$ is OMe.

In some embodiments, the compound of formula (I) is represented by a compound of formula (V)

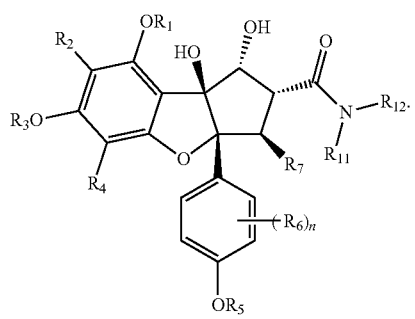
(V)
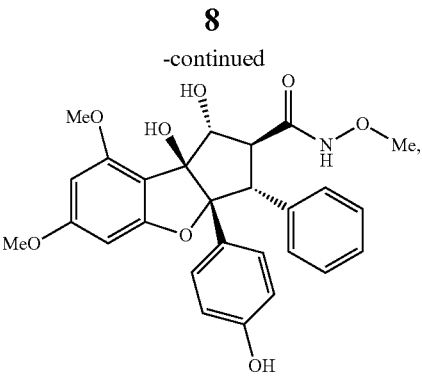
In some embodiments, the compound of formula (I) is a compound of formula (VI)
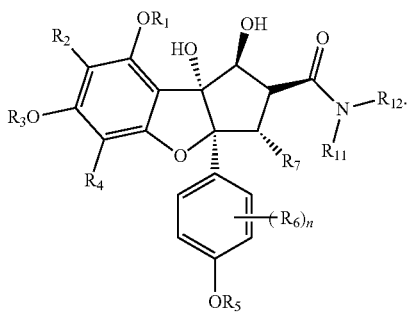
(VI)
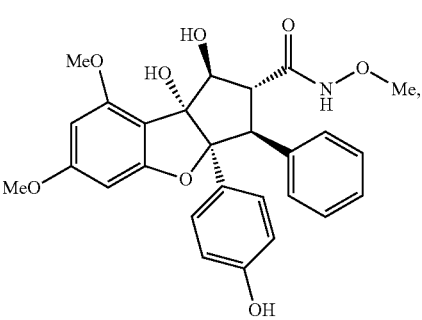
In some embodiments, the compound of formula (I) is
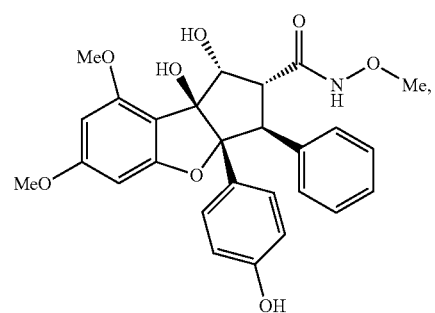
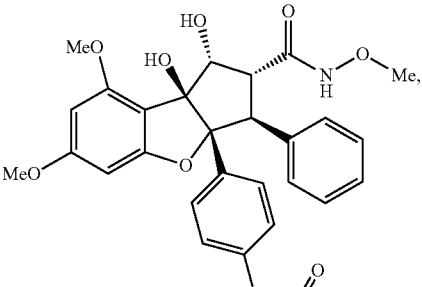
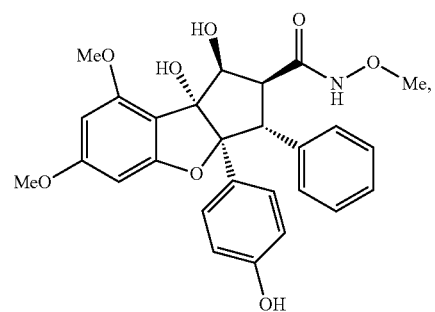
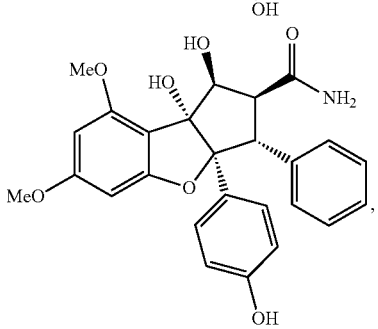

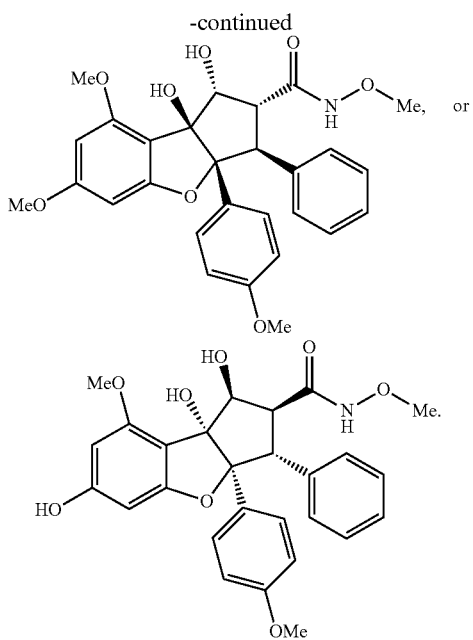

Unless defined otherwise, all technical and scientific terms used herein have the same meaning as commonly understood to one of ordinary skill in the art.

As used herein, in some embodiments, the term "alkyl" refers to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkyloxy" or "alkoxy" refers to an —O-alkyl group.

In some embodiments, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. A cycloalkyl group having one or more fused aromatic rings can be attached through the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like.

As used herein, "cycloalkyloxy" refers to an —O-cycloalkyl group.

As used herein, "cycloalkylalkyl" refers to an alkyl group substituted by a cycloalkyl group.

In some embodiments, an "cycloalkylalkyloxy" group refers to an —O-alkyl group substituted by a cycloalkyl group.

In some embodiments, "aryl" refers to monocyclic or polycyclic (e.g., having 2, 3 or 4 fused rings) aromatic hydrocarbons such as, for example, phenyl, naphthyl, anthracenyl, phenanthrenyl, and the like. In some embodiments, an aryl group has from 6 to about 20 carbon atoms. In some embodiments, "aryl" may be optionally substituted at any one or more positions.

As used herein, "aryloxy" refers to an —O-aryl group.

As used herein, "arylalkyl" refers to an alkyl group substituted by an aryl group.

As used herein, "arylalkyloxy" refers to an —O-alkyl group substituted by an aryl group.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR (as in N-substituted pyrrolidinyl)).

In some embodiments, "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms. In some embodiments, "heteroaryl" may be optionally substituted at any one or more positions capable of bearing a hydrogen atom.

The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, "heteroaryloxy" refers to an —O-heteroaryl group.

As used herein, "heteroarylalkyl" refers to an alkyl group substituted by a heteroaryl group.

As used herein, "heteroarylalkyloxy" refers to an —O-alkyl group substituted by a heteroaryl group.

In some embodiments, "heterocycloalkyl" refers to a non-aromatic heterocycle where one or more of the ring-forming atoms are a heteroatom such as an O, N, or S atom. Heterocycloalkyl groups can include mono- or polycyclic (e.g., having 2, 3 or 4 fused rings) ring systems as well as spirocycles. Example heterocycloalkyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with)

to the nonaromatic heterocyclic ring, for example phthalimidyl, naphthalimidyl, and benzo derivatives of heterocycles. A heterocycloalkyl group having one or more fused aromatic rings can be attached though either the aromatic or non-aromatic portion. Also included in the definition of heterocycloalkyl are moieties where one or more ring-forming atoms are substituted by 1 or 2 oxo or sulfido groups. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "heterocycloalkyloxy" refers to an —O-heterocycloalkyl group.

As used herein, "heterocycloalkylalkyl" refers to an alkyl group substituted by a heterocycloalkyl group.

As used herein, "heterocycloalkylalkyloxy" refers to an —O-alkyl group substituted by a heterocycloalkyl group.

In some embodiments, "halo" or "halogen" includes fluoro, chloro, bromo, and iodo. A "halogen-substitution" or "halo" substitution designates replacement of one or more hydrogen atoms with F, Cl, Br or I.

In some embodiments, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

It is understood that each of alkyl, cycloalkyl, heterocycloalkyl, aryl, and heteroaryl may be optionally substituted with independently selected groups such as alkyl, haloalkyl, hydroxyalkyl, aminoalkyl, carboxylic acid and derivatives thereof, including esters, amides, and nitrites, hydroxy, alkyloxy, acyloxy, amino, alky and dialkylamino, acylamino, thio, and the like, and combinations thereof.

In some embodiments, the term "substituted" refers to the replacement of a hydrogen moiety with a non-hydrogen moiety in a molecule or group. It can refer to "mono-substituted" or "poly-substituted." The term "mono-substituted" or "poly-substituted" means substituted with one or more than one substituent up to the valence of the substituted group. For example, a mono-substituted group can be substituted with 1 substituent, and a poly-substituted group can be substituted with 2, 3, 4, or 5 substituents. When a list of possible substituents is provided, the substituents can be independently selected from that group.

The term "optionally substituted," in some embodiments, refers to that the groups in question are either unsubstituted or substituted with one or more of the substituents specified. When the groups in question are substituted with more than one substituent, the substituents may be the same or different. Such other functional groups illustratively include, but are not limited to, amino, hydroxyl, CN, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, CH, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted. In some embodiments, the functional groups are the substituents described herein for any one of variables. Furthermore, when using the terms "independently," "independently are," and "independently selected from" mean that the groups in question may be the same or different. Certain of the herein defined terms may occur more than once in the structure, and upon such occurrence each term shall be defined independently of the other.

Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

In each of the foregoing and each of the following embodiments, it is to be understood that the formulas also include any and all hydrates and/or solvates of the compound formulas. It is appreciated that certain functional groups, such as the hydroxy, amino, and like groups form complexes and/or coordination compounds with water and/or various solvents, in the various physical forms of the compounds. Accordingly, the above formulas are to be understood to include and represent those various hydrates and/or solvates.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

Compounds described herein may contain one or more asymmetric centers and may thus give rise to diastereomers and optical isomers. The present invention includes all such possible optical isomers, diastereomers as well as their racemic mixtures, their substantially pure resolved enantiomers, all possible geometric isomers, and pharmaceutically acceptable salts thereof. The above Formula (I) is shown without a definitive stereochemistry at certain positions. The present invention includes all stereoisomers of Formula (I) and pharmaceutically acceptable salts thereof. Further, mixtures of stereoisomers as well as isolated specific stereoisomers are also included.

In some embodiments, the phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes "pharmaceutically acceptable salts" of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compound of the invention include the conventional non-toxic salts of the parent compound formed, for example, from non-toxic inorganic or organic acids. The pharmaceutically acceptable salts of the compound of the invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

The pharmaceutically acceptable salts of the compound of the invention can be also obtained by converting derivatives which possess tertiary amino groups into the corresponding quaternary ammonium salts in a manner known per se using quaternizing agents. Examples of suitable quaternizing agents are alkyl halides, such as methyl iodide, ethyl bromide, and n-propyl chloride, and also arylalkyl halides, such as benzyl chloride or 2-phenylethyl bromide. In some embodiments, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

Possible pharmaceutically acceptable salts are well known in the art. For example, S. M. Berge, et al. describe pharmaceutically acceptable salts in detail in *J. Pharmaceutical Sciences*, 66: 1-19, 1977; incorporated herein by reference.

Typically, a pharmaceutically acceptable salt form of a compound can be prepared in situ during the final isolation and purification of the compound, or separately by reacting the free base functionality with a suitable organic or inorganic acid. Examples of typical pharmaceutically acceptable, nontoxic acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods used in the art such as ion exchange.

Other pharmaceutically acceptable salts can include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and quaternary ammonium salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

This invention further includes derivatives of the compound of the invention. The term "derivatives" includes but is not limited to ether derivatives, acid derivatives, amide derivatives, ester derivatives and the like. In addition, this invention further includes hydrates or solvates of the compound of the invention. The term "hydrate" includes but is not limited to hemihydrate, monohydrate, dihydrate, trihydrate and the like.

This invention further includes metabolites of the compound of the invention. The term "metabolite" means any substance produced from another substance by metabolism or a metabolic process.

This invention further includes pharmaceutical products of the compound of the invention. The term "pharmaceutical product" means a composition suitable for pharmaceutical use (pharmaceutical composition), as defined herein.

This invention further includes prodrugs of the compound of the invention. The term "prodrug" means a substance which can be converted in vivo into a biologically active agent by such reactions as hydrolysis, esterification, de-esterification, activation, salt formation and the like.

This invention further includes crystals of the compound of the invention. Further, this invention provides polymorphs of the compound of the invention. The term "crystal" means a substance in a crystalline state. The term "polymorph" refers to a particular crystalline state of a substance, having particular physical properties such as X-ray diffraction, IR spectra, melting point, and the like.

The present invention further provides a method for preventing, treating or intervening in the recurrence of a cancer or dysproliferative disease in a subject comprising administering to the subject a compound of the invention as described herein, or a pharmaceutically acceptable salt thereof, or a pharmaceutical composition thereof.

Cancer includes but is not limited to cancerous and precancerous conditions, including, for example, premalignant and malignant hyperproliferative diseases such as cancers of the breast, ovary, germ cell, skin, prostate, colon, bladder, cervix, uterus, stomach, lung, esophagus, blood and lymphatic system, larynx, oral cavity, as well as metaplasias, dysplasias, neoplasias, leukoplakias and papillomas of the mucous membranes, and in the treatment of Kaposi's sarcoma. These are also referred to herein as dysproliferative diseases or dysproliferation.

In certain embodiments, the cancer is T-cell acute lymphoblastic leukemia (sometimes abbreviated T-ALL), small cell lung cancer, renal cell carcinoma, squamous cell carcinoma of the head and neck, neuroblastoma, pancreatic cancer, transformed follicular lymphoma, mantel cell lymphoma, breast cancer, ovarian cancer, hepatocellular carcinoma, non-small cell lung cancer, gastric cancer, Ewing sarcoma or lung adenocarcinoma.

In one embodiment, the compounds and uses embodied herein are directed to small cell lung cancer. In one embodiment, the compounds and uses embodied herein are directed to renal cancers. In one embodiment, the compounds and uses embodied herein are directed to neuroblastoma. In one embodiment, the compounds and uses embodied herein are directed to pancreatic cancers. In one embodiment the agent suppresses the growth of cancer cells in vitro or in vivo.

Dysproliferative diseases other than cancers include psoriasis, rheumatoid arthritis and other inflammatory joint and skin diseases, neovascularization of the eye, atherosclerosis, As noted herein, the compounds of the invention are inhibitors of protein translation and are useful for the treatment of cancer and other dysproliferative diseases. The biological activity of inventive compounds can be readily assessed in any of a number of in vitro and in vivo assays. Downregulation of oncogene expression such as but not limited to that of c-MYC, N-Myc, L-Myc, N-RAS, MYB, Notch1, BCL2, MDM2, CCDN1, MAF, MCL-1 and CDK6 can be performed using cancer cell lines. In cell-based reporter assays and in vitro translation assays, compounds can be shown to inhibit translation of eIF4A-dependent mRNA, while having little effect on eIF4A-independent translation. In vitro, activity against cancer cells can be assessed in a cell viability assay using leukemia cell lines such as KOPTK1 of MOLT-4 cells, and a non-tumor cell line such as MRC-5 can be used to assess selectivity. In vivo, various tumor models including xenograft models can be used to evaluate compounds. For example, the T-ALL murine cell line KOPTK-1 can be used. Primary cells can also be used. In one embodiment, delay in tumor growth, tumor cell apoptosis and cell cycle arrest can be shown in KOPTK-1 tumor bearing NOD/SCID mice. A pancreatic cancer model using PDAC cells (KRAS/p53-) can be used to show reduction in tumor volume. A small cell lung cancer line NCI-H82 can be employed. Using such in vitro studies and models, compounds of the invention have been shown to have potential to treat cancer.

Dysproliferative disorders refers in one embodiment to abnormal proliferation of cells, including hyperproliferative disorders, hyperplasia, metaplasia, dysplasia, by way of non-limiting examples, as described below.

In certain embodiments, compounds and compositions of the invention can be used to treat hyperproliferative disorders, including neoplasms. Examples of hyperproliferative disorders that can be treated by compounds and compositions of the invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, and urogenital tract.

Similarly, other hyperproliferative disorders can also be treated by compounds and compositions of the invention. Examples of such hyperproliferative disorders include, but are not limited to: acute childhood lymphoblastic leukemia, acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non Hodgkin's lymphoma, adult primary liver cancer, adult soft tissue sarcoma, AIDS related lymphoma, AIDS related malignancies, anal cancer, astrocytoma, bile duct cancer, bladder cancer, bone cancer, brain stem glioma, brain tumors, breast cancer, cancer of the renal pelvis and ureter, central nervous system (primary) lymphoma, central nervous system lymphoma, cerebellar astrocytoma, cerebral astrocytoma, cervical cancer, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood cerebral astrocytoma, childhood extracranial germ cell tumors, childhood Hodgkin's disease, childhood Hodgkin's lymphoma, childhood hypothalamic and visual pathway glioma, childhood lymphoblastic leukemia, childhood medulloblastoma, childhood non Hodgkin's lymphoma, childhood pineal and supratentorial primitive neuroectodermal tumors, childhood primary liver cancer, childhood rhabdomyosarcoma, childhood soft tissue sarcoma, childhood visual pathway and hypothalamic glioma, chronic lymphocytic leukemia, chronic myelogenous leukemia, colon cancer, cutaneous T cell lymphoma, endocrine pancreas islet cell carcinoma, endometrial cancer, ependymoma, epithelial cancer, esophageal cancer, Ewing's sarcoma and related tumors, exocrine pancreatic cancer, extracranial germ cell tumor, extragonadal germ cell tumor, extrahepatic bile duct cancer, eye cancer, female breast cancer, Gaucher's disease, gallbladder cancer, gastric cancer, gastrointestinal carcinoid tumor, gastrointestinal tumors, germ cell tumors, gestational trophoblastic tumor, hairy cell leukemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, kidney cancer, laryngeal cancer, lip and oral cavity cancer, liver cancer, lung cancer, lymphoproliferative disorders, macroglobulinemia, male breast cancer, malignant mesothelioma, malignant thymoma, medulloblastoma, melanoma, mesothelioma, metastatic occult primary squamous neck cancer, metastatic primary squamous neck cancer, metastatic squamous neck cancer, multiple myeloma, multiple myeloma/plasma cell neoplasm, myelodysplastic syndrome, myelogenous leukemia, myeloid leukemia, myeloproliferative disorders, nasal cavity and paranasal sinus cancer, nasopharyngeal cancer, neuroblastoma, non Hodgkin's lymphoma during pregnancy, nonmelanoma skin cancer, non small cell lung cancer, occult primary metastatic squamous neck cancer, oropharyngeal cancer, osteo/malignant fibrous sarcoma, osteosarcoma/malignant fibrous histiocytoma, osteosarcoma/malignant fibrous histiocytoma of bone, ovarian epithelial cancer, ovarian germ cell tumor, ovarian low malignant potential tumor, pancreatic cancer, paraproteinemias, purpura, parathyroid cancer, penile cancer, pheochromocytoma, pituitary tumor, plasma cell neoplasm/multiple myeloma, primary central nervous system lymphoma, primary liver cancer, prostate cancer, rectal cancer, renal cell cancer, renal pelvis and ureter cancer, retinoblastoma, rhabdomyosarcoma, salivary gland cancer, sarcoidosis sarcomas, Sezary syndrome, skin cancer, small cell lung cancer, small intestine cancer, soft tissue sarcoma, squamous neck cancer, stomach cancer, supratentorial primitive neuroectodermal and pineal tumors, T cell lymphoma, testicular cancer, thymoma, thyroid cancer, transitional cell cancer of the renal pelvis and ureter, transitional renal pelvis and ureter cancer, trophoblastic tumors, ureter and renal pelvis cell cancer, urethral cancer, uterine cancer, uterine Sarcoma, vaginal Cancer, visual pathway and hypothalamic glioma, vulvar cancer, Waldenstrom's macroglobulinemia, Wilms' tumor, and any other hyperproliferative disease, located in an organ system listed above.

In another embodiment, the compounds and compositions of the invention are used to prevent, and/or treat premalignant conditions and to prevent progression to a neoplastic or malignant state, including but not limited to those disorders described above. Such uses are indicated in conditions known to precede or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68 79).

Hyperplasia is a form of controlled cell proliferation, involving an increase in cell number in a tissue or organ, without significant alteration in structure or function. Hyperplastic disorders which can be prevented, and/or treated with compounds and compositions of the invention include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, focal epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia.

Metaplasia is a form of controlled cell growth in which one type of adult or fully differentiated cell substitutes for another type of adult cell. Metaplastic disorders which can be prevented, and/or treated with compounds and compositions of the invention include, but are not limited to, agnogenic myeloid metaplasia, apocrine metaplasia, atypical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, and symptomatic myeloid metaplasia.

Dysplasia is frequently a forerunner of cancer, and is found mainly in the epithelia; it is the most disorderly form of non neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation. Dysplastic disorders which can be prevented, and/or treated with compounds and compositions of the invention include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal retinal dysplasia, hidrotic ectodermal dysplasia, hypohidrotic ectodermal dysplasia, lymphopenic thymic dysplasia, mammary dysplasia, mandibulofacial dysplasia, metaphysical dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo optic dysplasia, spondyloepiphysial dysplasia, and ventriculoradial dysplasia.

Additional pre neoplastic disorders which can be prevented, and/or treated with compounds and compositions of the invention include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

In certain embodiments, the present invention relates to the aforementioned method, wherein said cancer or other dysproliferative disease is selected from the group consisting of leukemias, myeloid leukemias, lymphocytic leukemias, lymphomas, myeloproliferative diseases, solid tumors, sarcomas, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In certain embodiments, the present invention relates to the aforementioned method, wherein said cancer or other dysproliferative disease is selected from the group consisting of brain tumors, glioma, diabetic retinopathy, and pancreatic cancers.

In certain embodiments, the present invention relates to the aforementioned method, wherein said cancer or other dysproliferative disease is selected from the group consisting of arteriovenous (AV) malformations, psoriasis, benign prostatic hypertrophy, cutaneous fungal infections, warts, birthmarks, moles, nevi, skin tags, lipomas, angiomas, hemangiomas, and cutaneous lesions.

Another aspect of the invention related to a method for treating an inflammatory disease or disorder such as rheumatoid arthritis, in which, for example, inappropriate angiogenesis leads to the formation of pannus and associated pathology in a joint, or neovascularization from the retina in diabetic patients leading to blindness.

The present invention further provides a method for preventing, treating or intervening in the recurrence of fibrosis or a fibroproliferative disease in a subject comprising administering to the subject a compound of the invention as described herein, or a pharmaceutically acceptable salt thereof, or a pharmaceutical composition thereof.

Fibrosis or fibroproliferative conditions, disorders and diseases involve increased, excessive or inappropriate deposition of extracellular matrix in and around certain cells comprising tissues and organs, leading to cellular, tissue or organ dysfunction. In certain embodiments, fibrosis and fibroproliferative conditions, disorders and diseases include but are not limited to fibrotic liver disease, hepatic ischemia-reperfusion injury, hepatic disease including fibrosis and cirrhosis; liver fibrosis associated with hepatitis C, hepatitis B, delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency); cerebrovascular diseases such as cerebral infarction or stroke, amelioration of ischemia/reperfusion injury in the brain; heart and cardiovascular diseases such as ischemic heart disease, cardiac fibrosis, myocardial ischemia and atherosclerosis, amelioration of ischemia/reperfusion injury in the heart, normalization of myocardial perfusion as a consequence of chronic cardiac ischemia or myocardial infarction; renal diseases such as renal failure, renal fibrosis, radiocontrast nephropathy, fibrosis secondary to renal obstruction, renal trauma and transplantation, renal failure secondary to chronic diabetes and/or hypertension; and lung diseases such as lung (pulmonary) fibrosis and idiopathic pulmonary fibrosis.

In other embodiments, the fibrotic or fibroproliferative disease, disorder or condition is damaged and/or ischemic organs, transplants or grafts; ischemia/reperfusion injury; pancreatitis; scleroderma; systemic sclerosis; and dermal fibrosis. In still further embodiments, the compounds described herein are useful for acceleration of wound healing; reducing post-surgical scarring; reducing adhesion formation; improving vascularization of a damaged and/or ischemic organ, transplant or graft; development or augmentation of collateral vessel development after vascular occlusion or to ischemic tissues or organs; muscular dystrophy, amyotrophic lateral sclerosis, and/or diabetes mellitus.

Treatment of a human or mammalian subject with a compound of the invention for any one of the aforementioned conditions or diseases is typically achieved by administration of the compound in a pharmaceutical composition. The invention also encompasses a pharmaceutical composition that is comprised of a compound of Formula (I) in combination with a pharmaceutically acceptable carrier.

The term "inhibit" is used to mean decreasing the level of activity of, including decreasing the degree of interaction with one or more biologically relevant partners (e.g., substrates, co-factors, ligands or other entities) associated with a biological effect. In some embodiments, a biologically relevant partner is one which would associate in nature.

The terms "treat" or "treating," as used herein, refer to partially or completely alleviating, delaying onset of, reducing the incidence of, ameliorating and/or relieving a disorder, disease, or condition, or one or more symptoms of the disorder, disease or condition.

The term "patient" or "subject," as used herein, means a mammal to which a formulation or composition comprising a formulation is administered, and includes humans.

The term "substantially free of," as used herein, refers to containing no more than an insignificant amount. In some embodiments, a composition or preparation is "substantially free of a recited element if it contains less than 5%, 4%, 3%, 2%, or 1%, by weight of the element. In some embodiments, the composition or preparation contains less than 0.9%, 0.8%, 0.7%, 0.6%, 0.5%, 0.4%, 0.3%, 0.2%, 0.1% or less of the recited element. In some embodiments, the composition or preparation contains an undetectable amount of the recited element.

In practice, the compounds of the invention, for example, represented by Formula (I), or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration. e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non aqueous liquid, as an oil in water emulsion, or as a water in oil liquid emulsion.

In addition to the common dosage forms set out above, the compound represented by Formula (I), or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Solid medicinal forms can comprise inert components and carrier substances, such as calcium carbonate, calcium phosphate, sodium phosphate, lactose, starch, mannitol, alginates, gelatine, guar gum, magnesium stearate, aluminium stearate, methyl cellulose, talc, highly dispersed silicic acids, silicone oil, higher molecular weight fatty acids, (such as stearic acid), gelatine, agar agar or vegetable or animal fats and oils, or solid high molecular weight polymers (such as polyethylene glycol); preparations which are suitable for oral administration can comprise additional flavorings and/or sweetening agents, if desired.

Liquid medicinal forms can be sterilized and/or, where appropriate, comprise auxiliary substances, such as preservatives, stabilizers, wetting agents, penetrating agents, emulsifiers, spreading agents, solubilizers, salts, sugars or sugar alcohols for regulating the osmotic pressure or for buffering, and/or viscosity regulators. Examples of such additives are tartrate and citrate buffers, ethanol and sequestering agents (such as ethylenediaminetetraacetic acid and its nontoxic salts). High molecular weight polymers, such as liquid polyethylene oxides, microcrystalline celluloses, carboxymethyl celluloses, polyvinylpyrrolidones, dextrans or gelatine, are suitable for regulating the viscosity. Examples of solid carrier substances are starch, lactose, mannitol, methyl cellulose, talc, highly dispersed silicic acids, high molecular weight fatty acids (such as stearic acid), gelatine, agar agar, calcium phosphate, magnesium stearate, animal and vegetable fats, and solid high molecular weight polymers, such as polyethylene glycol.

Oily suspensions for parenteral or topical applications can be vegetable synthetic or semisynthetic oils, such as liquid fatty acid esters having in each case from 8 to 22 C atoms in the fatty acid chains, for example palmitic acid, lauric acid, tridecanoic acid, margaric acid, stearic acid, arachidic acid, myristic acid, behenic acid, pentadecanoic acid, linoleic acid, elaidic acid, brasidic acid, erucic acid or oleic acid, which are esterified with monohydric to trihydric alcohols having from 1 to 6 C atoms, such as methanol, ethanol, propanol, butanol, pentanol or their isomers, glycol or glycerol. Examples of such fatty acid esters are commercially available miglyols, isopropyl myristate, isopropyl palmitate, isopropyl stearate, PEG 6-capric acid, caprylic/capric acid esters of saturated fatty alcohols, polyoxyethylene glycerol trioleates, ethyl oleate, waxy fatty acid esters, such as artificial ducktail gland fat, coconut fatty acid isopropyl ester, oleyl oleate, decyl oleate, ethyl lactate, dibutyl phthalate, diisopropyl adipate, polyol fatty acid esters, inter alia. Silicone oils of differing viscosity, or fatty alcohols, such as isotridecyl alcohol, 2-octyldodecanol, cetylstearyl alcohol or oleyl alcohol, or fatty acids, such as oleic acid, are also suitable. It is furthermore possible to use vegetable oils, such as castor oil, almond oil, olive oil, sesame oil, cotton seed oil, groundnut oil or soybean oil.

Suitable solvents, gelatinizing agents and solubilizers are water or watermiscible solvents. Examples of suitable substances are alcohols, such as ethanol or isopropyl alcohol, benzyl alcohol, 2-octyldodecanol, polyethylene glycols, phthalates, adipates, propylene glycol, glycerol, di- or tripropylene glycol, waxes, methyl cellosolve, cellosolve, esters, morpholines, dioxane, dimethyl sulphoxide, dimethylformamide, tetrahydrofuran, cyclohexanone, etc.

Mixtures of gelatinizing agents and film-forming agents are also perfectly possible. In this case, use is made, in particular, of ionic macromolecules such as sodium carboxymethyl cellulose, polyacrylic acid, polymethacrylic acid and their salts, sodium amylopectin semiglycolate, alginic acid or propylene glycol alginate as the sodium salt, gum arabic, xanthan gum, guar gum or carrageenan. The following can be used as additional formulation aids: glycerol, paraffin of differing viscosity, triethanolamine, collagen, allantoin and novantisolic acid. Use of surfactants, emulsifiers or wetting agents, for example of Na lauryl sulphate, fatty alcohol ether sulphates, di-Na-N-lauryl-β-iminodipropionate, polyethoxylated castor oil or sorbitan monooleate, sorbitan monostearate, polysorbates (e.g. Tween), cetyl alcohol, lecithin, glycerol monostearate, polyoxyethylene stearate, alkylphenol polyglycol ethers, cetyltrimethylammonium chloride or mono-/dialkylpolyglycol ether orthophosphoric acid monoethanolamine salts can also be required for the formulation. Stabilizers, such as montmorillonites or colloidal silicic acids, for stabilizing emulsions or preventing the breakdown of active substances such as antioxidants, for example tocopherols or butylhydroxyanisole, or preservatives, such as p-hydroxybenzoic acid esters, can likewise be used for preparing the desired formulations.

Preparations for parenteral administration can be present in separate dose unit forms, such as ampoules or vials. Use is preferably made of solutions of the active compound, preferably aqueous solution and, in particular, isotonic solutions and also suspensions. These injection forms can be made available as ready-to-use preparations or only be prepared directly before use, by mixing the active compound, for example the lyophilisate, where appropriate containing other solid carrier substances, with the desired solvent or suspending agent.

Intranasal preparations can be present as aqueous or oily solutions or as aqueous or oily suspensions. They can also be present as lyophilisates which are prepared before use using the suitable solvent or suspending agent.

Inhalable preparations can present as powders, solutions or suspensions. Preferably, inhalable preparations are in the form of powders, e.g. as a mixture of the active ingredient with a suitable formulation aid such as lactose.

The preparations are produced, aliquoted and sealed under the customary antimicrobial and aseptic conditions.

Thus, the present invention further provides a pharmaceutical composition comprising a compound of the invention as described herein, or a pharmaceutically acceptable salt thereof, and a pharmaceutically acceptable carrier.

The term "carrier" refers to any chemical entity that can be incorporated into a composition containing an active agent (e.g., a compound of formula (I)) without interfering with the stability and/or activity of the agent. In some embodiments, the term "carrier" refers to a pharmaceutically acceptable carrier. An exemplary carrier herein is water.

As used herein, in some embodiments, "pharmaceutical composition" refers to therapeutically effective amounts of the compound of the invention together with suitable diluents, preservatives, solubilizers, emulsifiers, adjuvant and/or carriers.

Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal and oral. In some embodiments, the pharmaceutical composition is administered parenterally, paracancerally, transmucosally, transdermally, intramuscularly, intravenously, intradermally, subcutaneously, intraperitoneally, intraventricularly, intravaginally, intracranially and intratumorally.

As used herein, in some embodiments, the terms "therapeutically effective amount" and "effective amount" of an agent refer to an amount sufficient to provide a therapeutic benefit in the treatment, prevention and/or management of a disease, disorder, or condition, e.g., to delay onset of or minimize (e.g., reduce the incidence, frequency, and/or magnitude of) one or more symptoms associated with the disease, disorder or condition to be treated. Those of ordinary skill in the art will appreciate that, a composition may be said to contain a "therapeutically effective amount" of an agent if it contains an amount that is effective when administered as a single dose within the context of a therapeutic regimen. In some embodiments, a therapeutically effective amount is an amount that, when administered as part of a dosing regimen, is statistically likely to delay onset of or minimize (reduce the incidence and/or magnitude of) one or more symptoms or side effects of a disease, disorder or condition. In some embodiments, a "therapeutically effective amount" is an amount that enhances therapeutic efficacy of another agent with which the composition is administered in combination.

In some embodiments, a therapeutically effective amount for administration to a human corresponds to a reference amount (e.g., a therapeutically effective amount in an animal model such as a mouse model) adjusted for body surface area of a human as compared with body surface area of the animal model, as is known in the art (see, for example Reagan-Shaw et al., "Dose translation from animal to human studies revisited," The FASEB Journal 22: 659-661 (2007), the entirety of which is herein incorporated by reference). In some embodiments, the reference therapeutically effective amount is an amount that is therapeutically effective in an animal model (e.g., in a mouse model). In some embodiments, the reference therapeutically effective amount is within the range of about 0.01 mg/kg to about 500 mg/kg. In some embodiments, the reference therapeutically effective amount is within the range of about 0.01 mg/kg to about 0.1 mg/kg. In some embodiments, the reference therapeutically effective amount is within the range of about 0.1 mg/kg to about 0.5 mg/kg. In some embodiments, the reference therapeutically effective amount is within the range of about 0.5 mg/kg to about 1 mg/kg. In some embodiments, the reference therapeutically effective amount is within the range of about 1 mg/kg to about 2.5 mg/kg. In some embodiments, the reference therapeutically effective amount is within the range of about 2.5 mg/kg to about 10 mg/kg. In some embodiments, the reference therapeutically effective amount is within the range of about 10 mg/kg to about 50 mg/kg. In some embodiments, the reference therapeutically effective amount is within the range of about 50 mg/kg to about 100 mg/kg. In some embodiments, the reference therapeutically effective amount is within the range of about 100 mg/kg to about 250 mg/kg. In some embodiments, the reference therapeutically effective amount is within the range of about 250 mg/kg to about 500 mg/kg.

In some embodiments, the term "comprise" or grammatical forms thereof, refers to the inclusion of the indicated active agent, such as the compound of this invention, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components, which exert a therapeutic effect via a mechanism distinct from that of the indicated active ingredient. In some embodiments, the term "consisting essentially of" may refer to components, which exert a therapeutic effect and belong to a class of compounds distinct from that of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In some embodiments, the pharmaceutically acceptable carriers, adjuvants, or vehicles refer to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As used herein, the term "combination," "combined," and related terms refer to the simultaneous exposure of a subject to two or more therapeutic agents in accordance with this invention. It will be appreciated that two or more agents are considered to be administered "in combination" whenever a subject is simultaneously exposed to both (or more) of the agents. Each of the two or more agents may be administered according to a different schedule; it is not required that individual doses of different agents be administered at the same time, or in the same composition. Rather, so long as both (or more) agents remain in the subject's body, they are considered to be administered "in combination." For example, one or more doses of a compound of the present invention may be administered with another therapeutic agent simultaneously or sequentially in separate unit dosage forms or together in a single unit dosage form. Accordingly, in some embodiments, the present invention provides a single unit dosage form comprising a compound of formula (I), an additional therapeutic agent, and a pharmaceutically acceptable carrier, adjuvant, or vehicle.

The term "formulation" refers to a composition that includes at least one active agent (e.g., a compound of formula (I)) in combination with one or more carriers, excipients or other pharmaceutical additives for administration to a patient. In general, particular carriers, excipients and/or other pharmaceutical additives are selected in accordance with knowledge in the art to achieve a desired stability, release, distribution and/or activity of active agent(s).

The term "parenteral" as used herein includes subcutaneous, intravenous, intramuscular, intra-articular, intra-synovial, intrastemal, intrathecal, intrahepatic, intralesional and intracranial injection or infusion techniques. Formulations provided herein for parenteral administration are typically water or oil-based (e.g., aqueous or oleaginous) suspensions or solutions. Such formulations may be prepared according to techniques known in the art, for example using suitable dispersing, wetting agents or suspending agents. In some embodiments, such formulations are sterile injectable solutions or suspensions in a non-toxic parenterally acceptable diluent or solvent, for example as a solution in 1,3-butanediol. Among the acceptable vehicles and solvents that may be employed are water, Ringer's solution and isotonic sodium chloride solution. Alternatively or additionally, sterile, fixed oils are conventionally employed as a solvent or suspending medium.

In some embodiments, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non aqueous liquid, as an oil in water emulsion, or as a water in oil liquid emulsion. In addition to the common dosage forms set out above, the compound represented by Formula (I), or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of the invention, e.g., a compound represented by Formula (I). The compound of the invention, e.g., the compounds of Formula (I), or pharmaceutically acceptable salts thereof, can also be included in pharmaceutical compositions in combination with one or more other therapeutically active compounds.

The pharmaceutical carrier employed can be, for example, a solid, liquid, or gas.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Generally, dosage levels on the order of from about 0.01 mg/kg to about 150 mg/kg of body weight per day are useful in the treatment of the above indicated conditions, or alternatively about 0.5 mg to about 7 g per patient per day. For example, dermatological diseases and cancers may be effectively treated by the administration of from about 0.01 to 50 mg of the compound per kilogram of body weight per day, or alternatively about 0.5 mg to about 3.5 g per patient per day. It is understood, however, that the specific dose level for any particular patient will depend upon a variety of factors including the age, body weight, general health, sex, diet, time of administration, route of administration, rate of excretion, drug combination and the severity of the particular disease undergoing therapy.

The expression "unit dose" as used herein refers to a physically discrete unit of a formulation appropriate for a subject to be treated (e.g., for a single dose); each unit containing a predetermined quantity of an active agent selected to produce a desired therapeutic effect (it being understood that multiple doses may be required to achieve a desired or optimum effect), optionally together with a pharmaceutically acceptable carrier, which may be provided in a predetermined amount. The unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may contain a variety of components in addition to the therapeutic agent(s). For example, acceptable carriers (e.g., pharmaceutically acceptable carriers), diluents, stabilizers, buffers, preservatives, etc., may be included as described infra. It will be understood, however, that the total daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Accordingly, in another aspect of the present invention, pharmaceutical compositions are provided, which comprise any one or more of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved agent to treat the same or related indication, or it may be any one of a number of agents undergoing approval in the Food and Drug Administration that ultimately obtain approval for the treatment of any disorder related to dysproliferation. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro drug or other adduct or derivative of a compound of this invention which upon administration to a patient in need is capable of providing, directly or indirectly, a compound as otherwise described herein, or a metabolite or residue thereof.

Generally, dosage levels on the order of from about 0.01 mg/kg to about 1 50 mg/kg of body weight per day are useful in the treatment of the above indicated conditions, or alternatively about 0.5 mg to about 7 g per patient per day. For example, dermatological diseases and cancers may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

CR31B, as a racemic mixture, or its enantiomers (+)-CR31B and (−)-CR31B refer to the compounds as described in WO2011140334 as CR-1-31B, its enantiomers and racemic mixture, and synonymic variants thereof.

The following examples are presented in order to more fully illustrate the preferred embodiments of the invention. They should in no way be construed, however, as limiting the broad scope of the invention.

EXAMPLES

Example 1. Synthesis of (1R,2R,3S,3aR,8bS)-1,8b-dihydroxy-3a-(4-hydroxyphenyl)-N,6,8-trimethoxy-3-phenyl-2,3-dihydro-1Hcyclopenta[b]benzofuran-2-carboxamide (Compound 1), (1S,2S,3R,3aS,8bR)-1,8b-dihydroxy-3a-(4-hydroxyphenyl)-N,6,8-trimethoxy-3-phenyl-2,3-dihydro-1Hcyclopenta[b]benzofuran-2-carboxamide (Compound 2), (1R,2S,3R,3aR,8bS)-1,8b-dihydroxy-3a-(4-hydroxyphenyl)-N,6,8-trimethoxy-3-phenyl-2,3-dihydro-1Hcyclopenta[b]benzofuran-2-carboxamide (Compound 3), and (1S,2R,3S,3aS,8bR)-1,8b-dihydroxy-3a-(4-hydroxyphenyl)-N,6,8-trimethoxy-3-phenyl-2,3-dihydro-1Hcyclopenta[b]benzofuran-2-carboxamide (Compound 4)

Compounds 1-4 were synthesized following the scheme below.

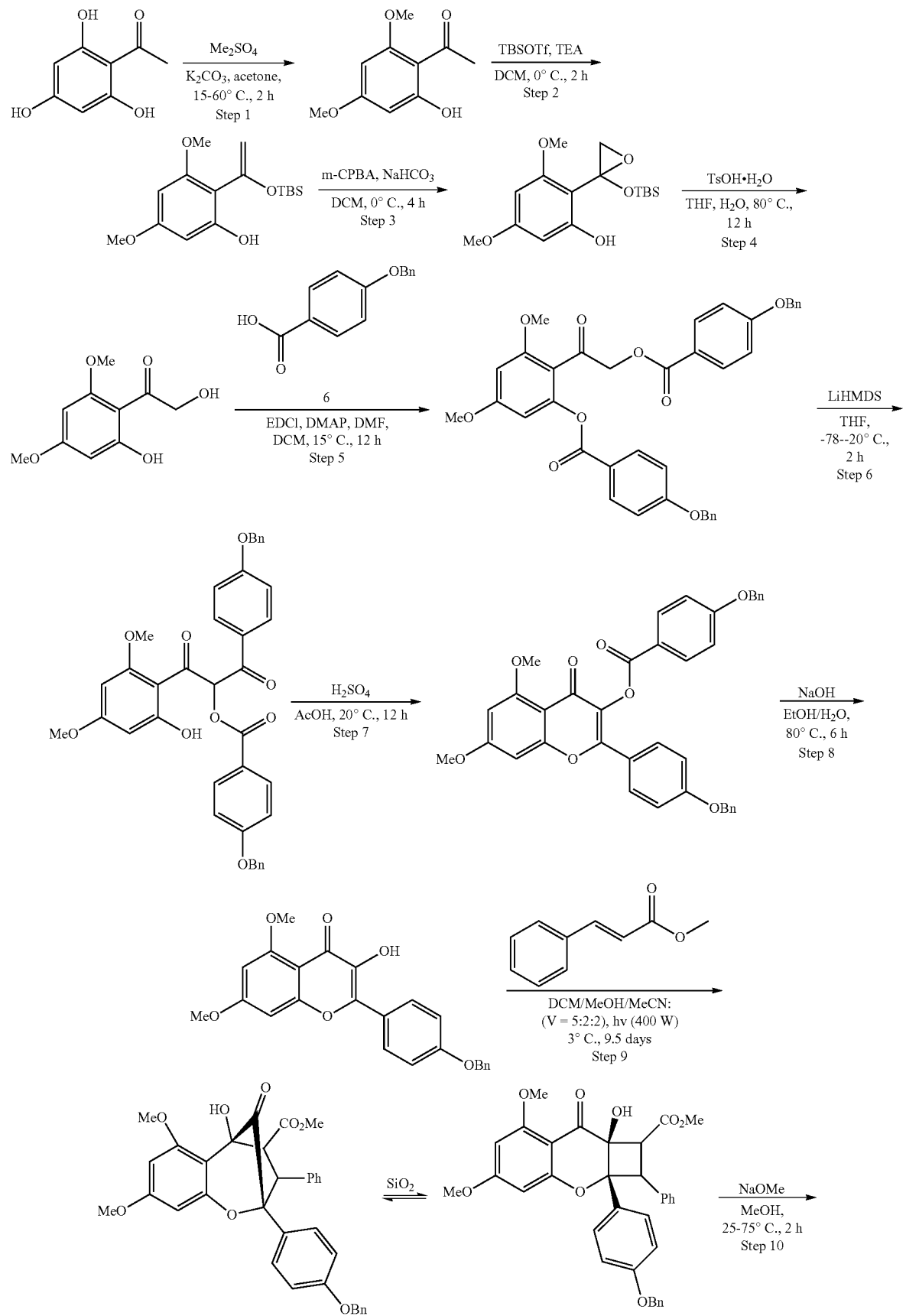

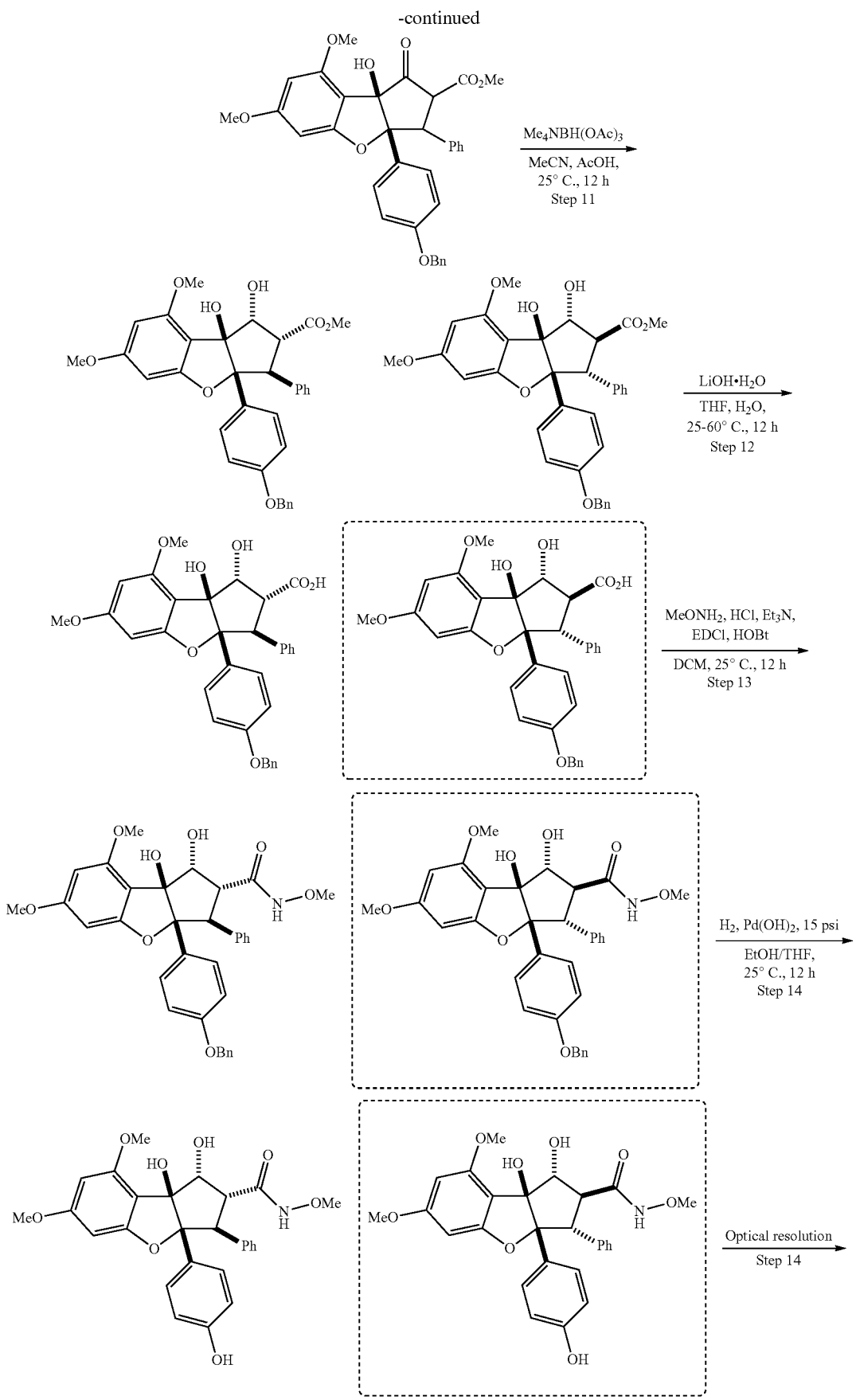

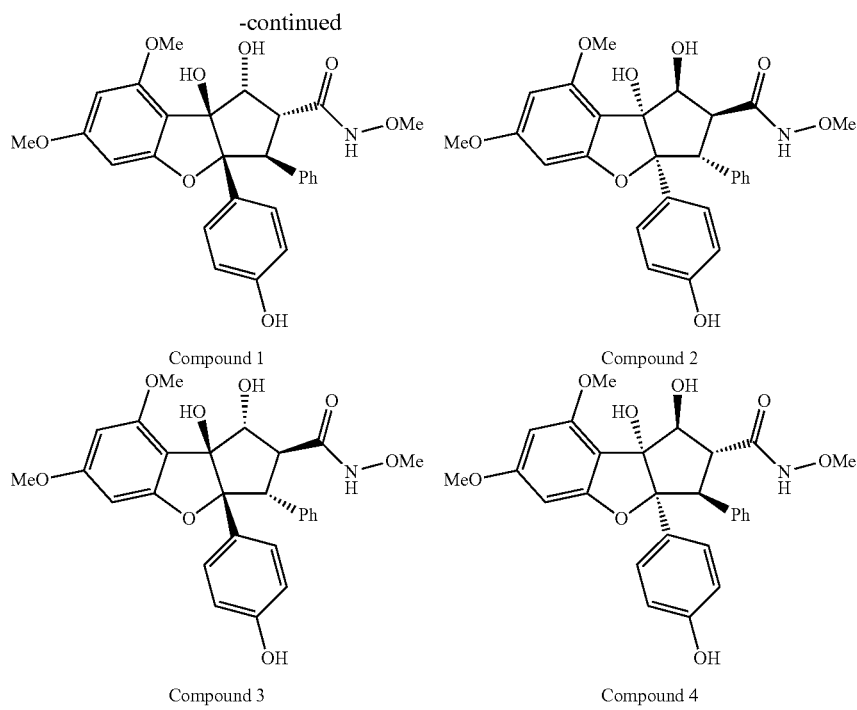

Compound 1

Compound 2

Compound 3

Compound 4

Step 1: 1-(2-hydroxy-4,6-dimethoxy-phenyl)ethanone

To a mixture of 1-(2,4,6-trihydroxyphenyl)ethanone (50 g, 297.36 mmol, 1 eq) and $K_2CO_3$ (102.74 g, 743.40 mmol, 2.5 eq) in acetone (500 mL) was added $Me_2SO_4$ (78.76 g, 624.46 mmol, 59.22 mL, 2.1 eq) at 15° C. The mixture was stirred at 60° C. for 2 h. The reaction mixture was filtered and the filter cake was washed with EtOAc (40 mL*3). The filtrate was concentrated under reduced pressure to give 1-(2-hydroxy-4,6-dimethoxy-phenyl)ethanone (53 g, crude) as gray solid. The product will be used directly in next step without further purification.

$^1$H NMR: ($CDCl_3$, 400 MHz) δ=14.01 (s, 1H), 6.06 (d, J=2.2 Hz, 1H), 5.92 (d, J=2.4 Hz, 1H), 3.86 (s, 3H), 3.82 (s, 3H), 2.61 (s, 3H).

Step 2: 2-[1-[tert-butyl(dimethyl)silyl]oxyvinyl]-3,5-dimethoxy-phenol

To a stirred solution of 1-(2-hydroxy-4,6-dimethoxy-phenyl)ethanone (53 g, 270.13 mmol, 1 eq) and TEA (82.00 g, 810.40 mmol, 112.80 mL, 3 eq) in DCM (600 mL) was added [tert-butyl(dimethyl)silyl]trifluoromethanesulfonate (142.81 g, 540.27 mmol, 124.18 mL, 2 eq) dropwise at 0° C. After the addition the reaction mixture was stirred at 0° C. for 2 h. The reaction mixture was diluted with water (500 mL) and concentrated under reduced pressure to remove the DCM. Then solution was extracted with EtOAc (200 mL*3). The organic layer was washed with brine (100 mL), dried over $Na_2SO_4$, filtered and the filtrate was concentrated under reduced pressure to give 2-[1-[tert-butyl(dimethyl)silyl]oxyvinyl]-3,5-dimethoxy-phenol (120 g, crude) as brown oil. The crude product was used directly in next step without further purification.

LCMS: (M+H+): 311.1 @1.874 min (5-95% ACN in $H_2O$, 2.0 min).

Step 3: 2-[2-[tert-butyl(dimethyl)silyl]oxyoxiran-2-yl]-3,5-dimethoxy-phenol To a mixture of 2-[1-[tert-butyl(dimethyl)silyl]oxyvinyl]-3,5-dimethoxy-phenol (120 g, 316.95 mmol, 1 eq) and $NaHCO_3$ (66.56 g, 792.37 mmol, 30.82 mL, 2.5 eq) in DCM (700 mL) was added m-CPBA (102.95 g, 507.12 mmol, 1.6 eq) at 0° C. in portions. After the addition, the mixture was stirred at 0° C. for 4 h, and then quenched by saturated aq. $Na_2SO_3$ (150 mL) and aq. $NaHCO_3$ (100 mL). The solution was stirred at room temperature for 0.5 h. After DCM was removed by evaporation. The residual aqueous phase was extracted with EtOAc (80 mL*4). The combined organic layer was washed with brine (150 mL), dried over Na2SO4, filtered and the filtrate was concentrated under reduced pressure to give 2-[2-[tert-butyl(dimethyl)silyl]oxyoxiran-2-yl]-3,5-dimethoxy-phenol (120 g, crude) as brown oil. The crude product was used directly in next step without further purification. LCMS: (M+H+): 327.1 @2.827 min (10-80% ACN in $H_2O$, 3.0 min).

Step 4: 2-hydroxy-1-(2-hydroxy-4,6-dimethoxy-phenyl)ethanone

To a solution of 2-[2-[tert-butyl(dimethyl)silyl]oxyoxiran-2-yl]-3,5-dimethoxy-phenol (120 g, 367.58 mmol, 1 eq) in THF (600 mL) and $H_2O$ (60 mL) was added p-toluenesulfonic acid monohydrate (6.99 g, 36.76 mmol, 0.1 eq) at 15° C. The mixture was stirred for 80° C. at 12 h, and then quenched by saturated $NaHCO_3$ solution (150 mL). Then the solution was concentrated under reduced pressure to remove THF. After that the mixture was filtered and the filter cake was collected. The collected solid were washed with water (20 mL*3) and EtOH (20 mL*5). Then the solid was dried under reduced pressure to give 2-hydroxy-1-(2-hydroxy-4,6-dimethoxy-phenyl)ethanone (22 g, 98.97 mmol, 26.92% yield, 95.46% purity) as gray solid.

LCMS: (M+H+): 213.0 @1.790 min (10-80% ACN in H$_2$O, 3.0 min).

$^1$H NMR: (CDCl$_3$, 400 MHz) δ=13.23 (s, 1H), 6.11 (d, J=2.2 Hz, 1H), 5.94 (d, J=2.3 Hz, 1H), 4.72 (d, J=4.8 Hz, 2H), 3.88 (s, 3H), 3.85 (s, 3H), 3.77 (t, J=4.8 Hz, 1H).

Step 5: [2-[2-(4-benzyloxybenzoyl)oxy-4,6-dimethoxy-phenyl]-2-oxo-ethyl]4-benzyloxybenzoate To a solution of 2-hydroxy-1-(2-hydroxy-4,6-dimethoxy-phenyl)ethanone (19 g, 89.54 mmol, 1 eq) in DCM (100 mL) and DMF (150 mL) was added 4-benzyloxybenzoic acid (62.35 g, 273.17 mmol, 3.05 eq), DMAP (3.72 g, 30.44 mmol, 0.34 eq) and 3-(ethyliminomethyleneamino)-N,N-dimethyl-propan-1-amine hydrochloride (77.24 g, 402.92 mmol, 4.5 eq) at 15° C. Then the reaction mixture was stirred at 15° C. for 12 h. The reaction mixture was poured into water (400 mL) and concentrated under reduced pressure to remove DCM. Then the resulting mixture was filtered and the filter cake was washed with H$_2$O (20 mL*3). The filter cake was collected and dried under reduced pressure. The collected solid was washed with EtOAc (20 mL*5). Then the solid was collected and dried by evaporation to give [2-[2-(4-benzyloxybenzoyl)oxy-4,6-dimethoxy-phenyl]-2-oxo-ethyl]4-benzyloxybenzoate (52 g, 73.97 mmol, 82.62% yield, 90% purity) as white solid.

$^1$H NMR: (CDCl$_3$, 400 MHz) δ=8.14-8.08 (m, 2H), 8.00-7.95 (m, 2H), 7.48-7.31 (m, 10H), 7.02 (d, J=8.9 Hz, 2H), 6.96 (d, J=8.9 Hz, 2H), 6.45 (d, J=2.2 Hz, 1H), 6.39 (d, J=2.1 Hz, 1H), 5.24 (s, 2H), 5.12 (d, J=11.0 Hz, 4H), 3.85 (d, J=6.7 Hz, 6H).

Step 6: [1-(4-benzyloxybenzoyl)-2-(2-hydroxy-4,6-dimethoxy-phenyl)-2-oxo-ethyl]4-benzyloxybenzoate To a solution of the [2-[2-(4-benzyloxybenzoyl)oxy-4,6-dimethoxy-phenyl]-2-oxo-ethyl]4-benzyloxybenzoate (20 g, 31.61 mmol, 1 eq) in THF (300 mL) at −78° C. under nitrogen was added dropwise LiHMDS (1 M, 96.00 mL, 3.04 eq). The mixture was stirred at−78° C. for 1 h and then stirred at −20° C. for 1 h. The mixture was poured into saturated aqueous NH4Cl solution (300 mL). The aqueous phase was extracted with ethyl acetate (100 mL*3). The combined organic phases were washed with brine (100 mL), dried over Na2SO4, filtered and concentrated in vacuum to give [1-(4-benzyloxybenzoyl)-2-(2-hydroxy-4,6-dimethoxy-phenyl)-2-oxo-ethyl]4-benzyloxybenzoate (20 g, crude) as gray solid. The crude product was used directly in next step without further purification.

$^1$H NMR: (CDCl$_3$, 400 MHz) δ=13.31 (s, 1H), 8.08 (d, J=8.8 Hz, 2H), 8.01 (d, J=8.8 Hz, 2H), 7.46-7.31 (m, 11H), 7.07 (d, J=8.8 Hz, 2H), 6.99 (d, J=8.8 Hz, 2H), 6.12 (d, J=2.2 Hz, 1H), 5.83 (d, J=2.2 Hz, 1H), 5.14 (d, J=6.6 Hz, 4H), 3.82 (s, 3H), 3.34 (s, 3H).

Step 7: [2-(4-benzyloxyphenyl)-5,7-dimethoxy-4-oxo-chromen-3-yl]4-benzyloxy benzoate To a stirred solution of [1-(4-benzyloxybenzoyl)-2-(2-hydroxy-4,6-dimethoxy-phenyl)-2-oxo-ethyl]4-benzyloxy-benzoate (20 g, 31.61 mmol, 1 eq) in AcOH (200 mL) was added H2SO4 (15.83 g, 158.18 mmol, 8.60 mL, 98% purity, 5 eq) dropwise at 20° C. Then the mixture was stirred at 20° C. for 12 h. The reaction mixture was quenched with cooled water (200 mL) and filtered. The filter cake was washed with EtOH (40 mL*3). Then the filter cake was collected and dried under reduced pressure to give [2-(4-benzyloxyphenyl)-5,7-dimethoxy-4-oxo-chromen-3-yl]4-benzyloxy benzoate (16 g, crude) as gray solid.

$^1$H NMR: (CDCl$_3$, 400 MHz) δ=8.07 (d, J=8.8 Hz, 2H), 7.79 (d, J=8.9 Hz, 2H), 7.40-7.21 (m, 10H), 6.93 (t, J=8.9 Hz, 4H), 6.45 (d, J=2.2 Hz, 1H), 6.26 (d, J=2.2 Hz, 1H), 5.06 (s, 2H), 4.99 (s, 2H), 3.81 (d, J=3.3 Hz, 6H).

Step 8: 2-(4-benzyloxyphenyl)-3-hydroxy-5,7-dimethoxy-chromen-4-one

To a stirred solution of [2-(4-benzyloxyphenyl)-5,7-dimethoxy-4-oxo-chromen-3-yl]4-benzyloxybenzoate (16 g, 26.03 mmol, 1 eq) in EtOH (160 mL) and H$_2$O (40 mL) was added NaOH (4.16 g, 104.13 mmol, 4 eq), then the mixture was heated to 80° C. and stirred for 6 h. The reaction mixture was diluted with water (300 mL) and the solution was acidified to pH=4 with aq. HCl (2 N). The resulting mixture was filtered and the filter cake was washed with EtOH (20 mL*10). The filter cake was collected and dried under vacuum to give 2-(4-benzyloxyphenyl)-3-hydroxy-5,7-dimethoxy-chromen-4-one (9 g, crude) as light yellow solid.

LCMS: (M+H+): 405.1 @1.536 min (10-90% ACN in H$_2$O, 2.0 min).

$^1$H NMR: (CDCl$_3$, 400 MHz) δ=8.17 (d, J=8.7 Hz, 2H), 7.52-7.31 (m, 6H), 7.10 (d, J=8.7 Hz, 2H), 6.52 (s, 1H), 6.33 (s, 1H), 5.14 (s, 2H), 3.96 (s, 3H), 3.90 (s, 3H).

Step 9

To a solution of 2-(4-benzyloxyphenyl)-3-hydroxy-5,7-dimethoxy-chromen-4-one (8.5 g, 21.02 mmol, 1 eq) in DCM (850 mL), MeCN (340 mL) and MeOH (340 mL) was added methyl (E)-3-phenylprop-2-enoate (34.1 g, 210.25 mmol, 10 eq) at 3° C. The mixture was stirred and irradiated (mercury lamp radiation (400 W)) under N$_2$ at 3° C. for 9.5 days. The reaction mixture was poured into ice water (1000 mL) and the organic phases were separated. The aqueous phase was back extracted with DCM (200 mL*3). The organic layer was washed with brine (600 mL), dried over Na$_2$SO$_4$, filtered and the filtrate was concentrated under reduced pressure. The residue was purified by column chromatography (SiO2, Petroleum ether/Ethyl acetate=10/1 to 5/1 to 1/1) to give the desired product (8 g, 6.85 mmol, 32.58% yield, 97% purity) as yellow solid. Due to the tautomerism, two peaks with M-17 were detected by LCMS.

LCMS: (M-17): 549.4 @1.321, 1.371 min (10-90% ACN in H$_2$O, 2.0 min).

Step 10

To a stirred solution of NaOMe (3.84 g, 21.32 mmol, 30% purity, 3.02 eq) in MeOH (30 mL) was added a solution of the product being obtained in the step 9 (8 g, 7.06 mmol, 1 eq) in MeOH (50 mL) at 25° C. After the addition the reaction mixture was heated to 75° C. and stirred for 2 h. The reaction was filtered after it was cooled to room temperature. The filter cake was suspended in saturated aq. NH$_4$Cl (100 mL) and the solution was extracted with EtOAc (30 mL*5). The organic layer was washed with brine (60 mL), dried over Na2SO4, filtered and the filtrate was concentrated under reduced pressure to afford the crude product (batch 1: 2.6 g). The filtrate was concentrated under reduced pressure. The residue from the concentrated filtrate was purified by column chromatography (SiO$_2$, Petroleum ether/Ethyl acetate=10/1 to 1/1) to give the second batch of the product (4 g). But it was still not pure after purification and used directly in next step without further purification.

LCMS: (batch 1), (M-17): 549.1@1.338; 549.0@1.398 min (10-90% ACN in H$_2$O, 2.0 min).

LCMS: (batch 2), (M-17): 549.0@1.320 min (10-90% ACN in H$_2$O, 2.0 min).

Step 11: Methyl (1R,3aR,8bS)-3a-(4-benzyloxyphenyl)-1,8b-dihydroxy-6,8-dimethoxy-3-phenyl-2,3-dihydro-1Hcyclopenta[b]benzofuran-2-carboxylate To a stirred solution of methyl (3aR,8bR)-3a-(4-benzyloxyphenyl)-8b-hydroxy-6,8-dimethoxy-1-oxo-3-phenyl-2,3-dihydrocyclopenta[b]benzofuran-2-carboxylate (4 g, 7.06 mmol, 1 eq) and AcOH (4.24 g, 70.60 mmol, 4.04 mL, 10 eq) in MeCN (30 mL) was added tetramethylammonium triacetoxyborohydride (11.14 g, 42.36 mmol, 6 eq). Then the mixture was stirred at 25° C. for 12 h. The reaction mixture was poured into ice-water (50 mL). The aqueous phase was extracted with ethyl acetate (30 mL*3). The combined organic phases were washed with brine (40 mL), dried over anhydrous Na$_2$SO$_4$, filtered and concentrated in vacuum to give methyl (1R,3aR,8bS)-3a-(4-benzyloxyphenyl)-1,8b-dihydroxy-6,8-dimethoxy-3-phenyl-2,3-dihydro-1Hcyclopenta[b]benzofuran-2-carboxylate (4 g, crude) was obtained as light yellow solid. The crude product was used directly in next step without further purification.

LCMS: (M-17): 551.4@1.296 min (10-90% ACN in H$_2$O, 2.0 min).

Step 12: (1R,3aR,8bS)-3a-(4-benzyloxyphenyl)-1,8b-dihydroxy-6,8-dimethoxy-3-phenyl-2,3-dihydro-1H-cyclopenta[b]benzofuran-2-carboxylic acid To a solution of the methyl (1R,3aR,8bS)-3a-(4-benzyloxyphenyl)-1,8b-dihydroxy-6,8-dimethoxy-3-phenyl-2,3-dihydro-1Hcyclopenta[b]benzofuran-2-carboxylate (4 g, 7.03 mmol, 1 eq) in THF (40 mL) and H$_2$O (10 mL) was added LiOH·H$_2$O (1.18 g, 28.12 mmol, 4.00 eq) at 25° C. The solution was stirred at 60° C. for 12 hours. The reaction mixture was diluted with water (50 mL). The solution was adjusted to pH=3 with aq HCl (2 N). Then the solution was extracted with EtOAc (30 mL*3). The combined organic layer was washed with brine (40 mL), dried over Na2SO4, filtered and the filtrated was concentrated under reduced pressure to afford (1R,3aR,8bS)-3a-(4-benzyloxyphenyl)-1,8b-dihydroxy-6,8-dimethoxy-3-phenyl-2,3-dihydro-1H-cyclopenta[b]benzofuran-2-carboxylic acid (3.1 g, crude) d as light yellow solid. The crude product was used directly in next step without further purification.

Step 13: (1R,3aR,8bS)-3a-(4-benzyloxyphenyl)-1,8b-dihydroxy-N,6,8-trimethoxy-3-phenyl-2,3-dihydro-1H-cyclopenta[b]benzofuran-2-carboxamide To a solution of (1R,3aR,8bS)-3a-(4-benzyloxyphenyl)-1,8b-dihydroxy-6,8-dimethoxy-3-phenyl-2,3-dihydro-1Hcyclopenta[b]benzofuran-2-carboxylic acid (3.1 g, 5.59 mmol, 1 eq), O-methylhydroxylamine hydrochloride (1.40 g, 16.76 mmol, 1.27 mL, 3.00 eq) in DCM (40 mL) was added HOBt (1.13 g, 8.39 mmol, 1.5 eq), EDCI (1.28 g, 6.70 mmol, 1.2 eq) and TEA (2.54 g, 25.12 mmol, 3.50 mL, 4.49 eq) at 25° C. under nitrogen. Then the mixture was stirred at 25° C. for 12 h. The reaction mixture was diluted with water (50 mL). The solution was extracted with DCM (30 mL*4). The organic layer was washed with brine (40 mL), dried over Na$_2$SO$_4$, filtered and the filtrate was concentrated under reduced pressure. The residue was purified by column chromatography (SiO2, Petroleum ether/Ethyl acetate=1/1 to 1/4) to give (1R,3aR,8bS)-3a-(4-benzyloxyphenyl)-1,8b-dihydroxy-N,6,8-trimethoxy-3-phenyl-2,3-dihydro-1H-cyclopenta[b]benzofuran-2-carboxamide (0.7 g, 1.18 mmol, 21.07% yield, 98.2% purity) as light yellow solid. SFC showed there were four isomers (method: IC-3_MeOH_I-PAm_10-40_Gradient_4 ml. Retention time: 3.54; 3.72; 4.03; 4.28).

LCMS: (M+H+): 584.2@1.173 min (10-90% ACN in H$_2$O, 2.0 min).

SFC: (Retention time: 3.54; 3.72; 4.03; 4.28).

Step 14

To a solution of (1R,3aR,8bS)-3a-(4-benzyloxyphenyl)-1,8b-dihydroxy-N,6,8-trimethoxy-3-phenyl-2,3-dihydro-1Hcyclopenta[b]benzofuran-2-carboxamide (750 mg, 1.29 mmol, 1 eq) in EtOH (5 mL) and THF (5 mL) was added Pd(OH)$_2$/C (0.5 g, 1.29 mmol, 20% purity) under N$_2$. The suspension was degassed under vacuum and purged with H2 three times. The mixture was stirred under H$_2$ (15 psi) at 25° C. for 8 h. The reaction mixture was filtered through a pad of Celite and the filter cake was washed with THF (20 mL×5). The filtrate was concentrated under reduced pressure to afford the crude product. The residue was checked by HPLC and Chiral SFC (Retention time: P1: 2.83 min; P2: 3.12 min; P3: 3.32 min; P4: 4.53 min).

Then the residue was separated by SFC (Instrument: Thar SFC80 preparative SFC; Column: Chiralpak AD-H 250*30 mm i.d. 5u; Mobile phase: A for CO$_2$ and B for IPA(0.1% NH3H2O); Gradient: B %=42%; Flow rate: 70 g/min; Wavelength: 220 nm; Column temperature: 40° C.; System back pressure: 100 bar) to give compounds 1-4.

Compound 1:

(1R,2R,3S,3aR,8bS)-1,8b-dihydroxy-3a-(4-hydroxyphenyl)-N,6,8-trimethoxy-3-phenyl-2,3-dihydro-1Hcyclopenta[b]benzofuran-2-carboxamide (125.7 mg, 238.38 μmol, 18.55% yield, 93.59% purity, 100% ee) was obtained as white solid.

LCMS: (M+H+): 494.1@1.562 min (25-100% ACN in H$_2$O, 4.5 min).

$^1$H NMR: (DMSO, 400 MHz) δ 11.11 (br s, 1H), 9.28 (br s, 1H), 7.15-7.07 (m, 5H), 6.92 (dd, J=2.3, 7.1 Hz, 2H), 6.69 (d, J=8.7 Hz, 2H), 6.14 (d, J=1.8 Hz, 1H), 6.09 (d, J=2.0 Hz, 1H), 5.03 (br s, 1H), 4.84 (br s, 1H), 4.44 (d, J=10.1 Hz, 1H), 3.78 (d, J=12.7 Hz, 1H), 3.74 (s, 3H), 3.69 (s, 3H), 3.36-3.33 (m, 3H), 2.72 (dd, J=10.4, 12.5 Hz, 1H).

SFC: (Retention time: 2.78; 100% ee).

Compound 2:

(1S,2S,3R,3aS,8bR)-1,8b-dihydroxy-3a-(4-hydroxyphenyl)-N,6,8-trimethoxy-3-phenyl-2,3-dihydro-1Hcyclopenta[b]benzofuran-2-carboxamide (92.4 mg, 185.29 μmol, 14.42% yield, 98.96% purity, 97.72% ee) was obtained as white solid.

LCMS: (M+H+): 494.1@2.283 min (10-80% ACN in H$_2$O, 4.5 min).

$^1$H NMR: (DMSO, 400 MHz) δ=11.11 (s, 1H), 9.26 (s, 1H), 7.15-7.06 (m, 5H), 6.91 (dd, J=2.3, 7.0 Hz, 2H), 6.69 (d, J=8.7 Hz, 2H), 6.14 (d, J=2.0 Hz, 1H), 6.08 (d, J=2.0 Hz, 1H), 5.02 (s, 1H), 4.83 (d, J=4.2 Hz, 1H), 4.43 (dd, J=4.2, 10.2 Hz, 1H), 3.77 (d, J=12.7 Hz, 1H), 3.74 (s, 3H), 3.69 (s, 3H), 3.33 (s, 3H), 2.74-2.66 (m, 1H).

SFC: (Retention time: 3.03; 97.72% ee).

Compound 3:

SFC showed the ee % value of P3 was 57%, so P3 was separated by SFC (Instrument: Thar SFC80 preparative SFC; Column: Chiralpak AD-H 250*30 mm id. 5u; Mobile phase: A for CO2 and B for IPA(0.1% NH3H2O); Gradient: B %=42%; Flow rate: 70 g/min; Wavelength: 220 nm; Column temperature: 40° C.; System back pressure: 100 bar) again to give (1R,2S,3R,3aR,8bS)-1,8b-dihydroxy-3a-(4-hydroxyphenyl)-N,6,8-trimethoxy-3-phenyl-2,3-dihydro-1Hcyclopenta[b]benzofuran-2-carboxamide (43 mg, 86.17 μmol, 6.71% yield, 98.9% purity, 100% ee) as white solid.

LCMS: (M+H+): 494.1@2.310 min (10-80% ACN in H$_2$O, 4.5 min).

$^1$H NMR: (DMSO, 400 MHz) δ 11.12 (br s, 1H), 9.02 (s, 1H), 7.07-7.01 (m, 2H), 7.00-6.95 (m, 1H), 6.91-6.84 (m, 4H), 6.41 (d, J=8.4 Hz, 2H), 6.26 (s, 1H), 6.11 (s, 1H), 4.94 (s, 1H), 4.60 (d, J=3.7 Hz, 1H), 4.55 (br s, 1H), 4.13 (d, J=14.1 Hz, 1H), 3.78 (s, 3H), 3.74 (s, 3H), 3.54 (dd, J=5.0, 13.8 Hz, 1H), 3.48 (s, 3H).

SFC: (Retention time: 2.43; 100% ee).

Optical rotation: (−52.86°±7.37°; c=0.5 g/100 mL diluted with methanol, 20° C.).

Compound 4:

The product was re-purified by prep-HPLC (column: Agela Durashell C18 150*25 5u; mobile phase: [water(10 mM NH4HCO3)-ACN]; B %: 30%-50%, 10 min) to give (1S,2R,3S,3aS,8bR)-1,8b-dihydroxy-3a-(4-hydroxyphenyl)-N,6,8-trimethoxy-3-phenyl-2,3-dihydro-1Hcyclopenta[b]benzofuran-2-carboxamide (30.5 mg, 61.80 μmol, 4.81% yield, 100% purity, 98.52% ee) as white solid.

LCMS: (M+H+): 494.1@2.323 min (10-80% ACN in H$_2$O, 4.5 min).

$^1$H NMR: (DMSO, 400 MHz) δ=11.12 (br s, 1H), 9.04 (s, 1H), 7.08-7.01 (m, 2H), 7.00-6.94 (m, 1H), 6.91-6.84 (m, 4H), 6.41 (d, J=8.6 Hz, 2H), 6.26 (d, J=1.7 Hz, 1H), 6.11 (d, J=1.7 Hz, 1H), 4.95 (s, 1H), 4.61 (d, J=3.8 Hz, 1H), 4.57-4.52 (m, 1H), 4.13 (d, J=14.1 Hz, 1H), 3.77 (s, 3H), 3.74 (s, 3H), 3.54 (dd, J=5.7, 14.1 Hz, 1H), 3.48 (s, 3H).

SFC: (Retention time: 3.69; 98.52% ee).

Optical rotation: (54.23°±8.95°; c=0.5 g/100 mL diluted with methanol, 20° C.).

Example 2. Synthesis of sodium 4-((1R,2R,3S,3aR,8bS)-1,8b-dihydroxy-6,8-dimethoxy-2-(methoxycarbamoyl)-3-phenyl-2,3,3a,8b-tetrahydro-1H-cyclopenta[b]benzofuran-3a-yl)phenyl phosphate (Compound 5)

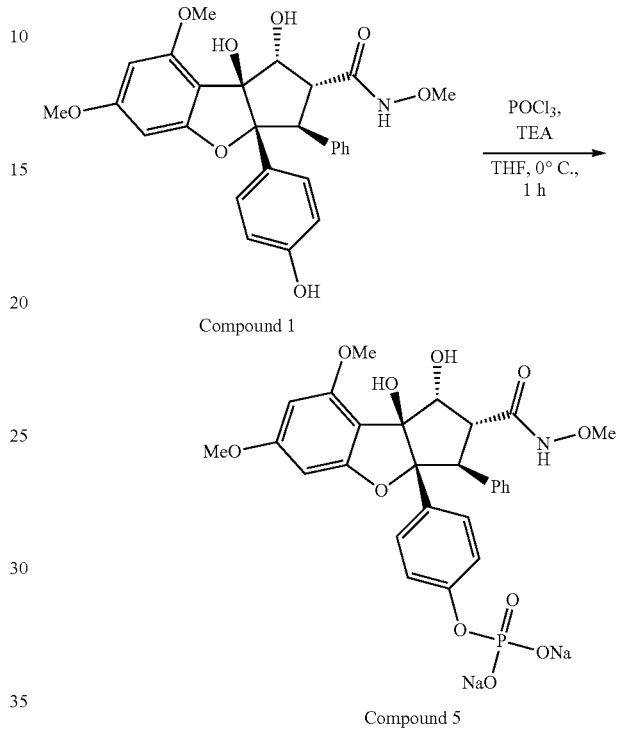

To a stirred solution of (1R,2R,3S,3aR,8bS)-1,8b-dihydroxy-3a-(4-hydroxyphenyl)-N,6,8-trimethoxy-3-phenyl-2,3-dihydro-1Hcyclopenta[b]benzofuran-2-carboxamide (43 mg, 87.13 μmol, 1 eq) in THF (5 mL) was added TEA (26 mg, 256.94 μmol, 35.76 μL, 2.95 eq) and POCl$_3$ (67 mg, 436.96 μmol, 40.61 μL, 5.01 eq) at 0° C. Then the mixture was stirred at 0° C. for 1 h. The reaction mixture was added slowly into aq. saturated NaHCO$_3$ solution (2 mL). The solution was extracted with EtOAc (1 mL*2). The organic layer was discarded. The aqueous phase was purified by neutral prep-HPLC (column: Waters Xbridge 150*25 5u; mobile phase: [Water-ACN]; B %: 1%-15%, 11 min) to give sodium 4-((1R,2R,3S,3aR,8bS)-1,8b-dihydroxy-6,8-dimethoxy-2-(methoxycarbamoyl)-3-phenyl-2,3,3a,8b-tetrahydro-1H-cyclopenta[b]benzofuran-3a-yl)phenyl phosphate (18.2 mg, 31.74 μmol, 36.42% yield, 100% purity) was obtained as light yellow solid.

LCMS: (M+H+): 574.2@2.041 min (10-80% ACN in H$_2$O, 4.5 min).

$^1$H NMR: (400 MHz, DEUTERIUM OXIDE) δ 7.19-7.11 (m, 4H), 7.09-7.01 (m, 3H), 6.85 (d, J=8.6 Hz, 2H), 6.34 (d, J=1.5 Hz, 1H), 6.20 (s, 1H), 4.59 (d, J=5.1 Hz, 1H), 4.35 (d, J=14.4 Hz, 1H), 3.85-3.79 (m, 4H), 3.75 (s, 3H), 3.57 (s, 3H).

SFC: (Retention time: 1.85; % ee: 100%).

Optical rotation: (−83.13°±8.95°; c=0.5 g/100 mL diluted with water, 20° C.).

Example 3. Synthesis of (1R,2R,3S,3aR,8bS)-1,6, 8b-trihydroxy-N,8-dimethoxy-3a-(4-methoxyphenyl)-3-phenyl-2,3-dihydro-1Hcyclopenta[b]benzofuran-2-carboxamide (Compound 6) and (1S,2S,3R, 3aS,8bR)-1,6,8b-trihydroxy-N,8-dimethoxy-3a-(4-methoxyphenyl)-3-phenyl-2,3,3a,8b-tetrahydro-1H-cyclopenta[b]benzofuran-2-carboxamide (Compound 7)
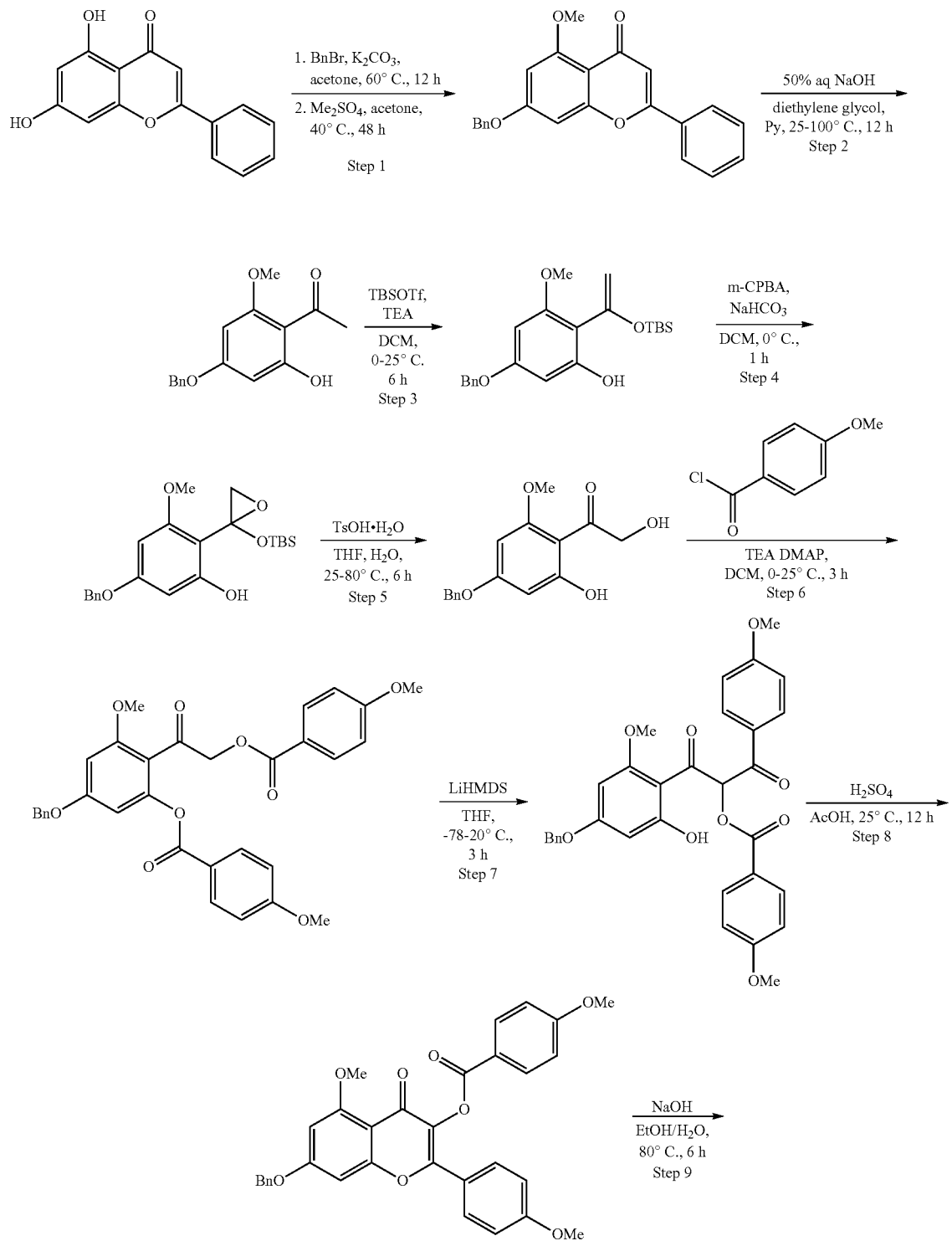

-continued
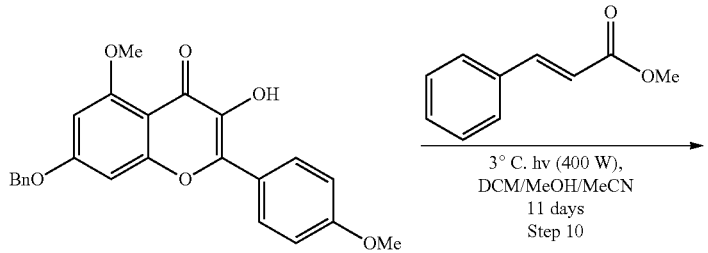
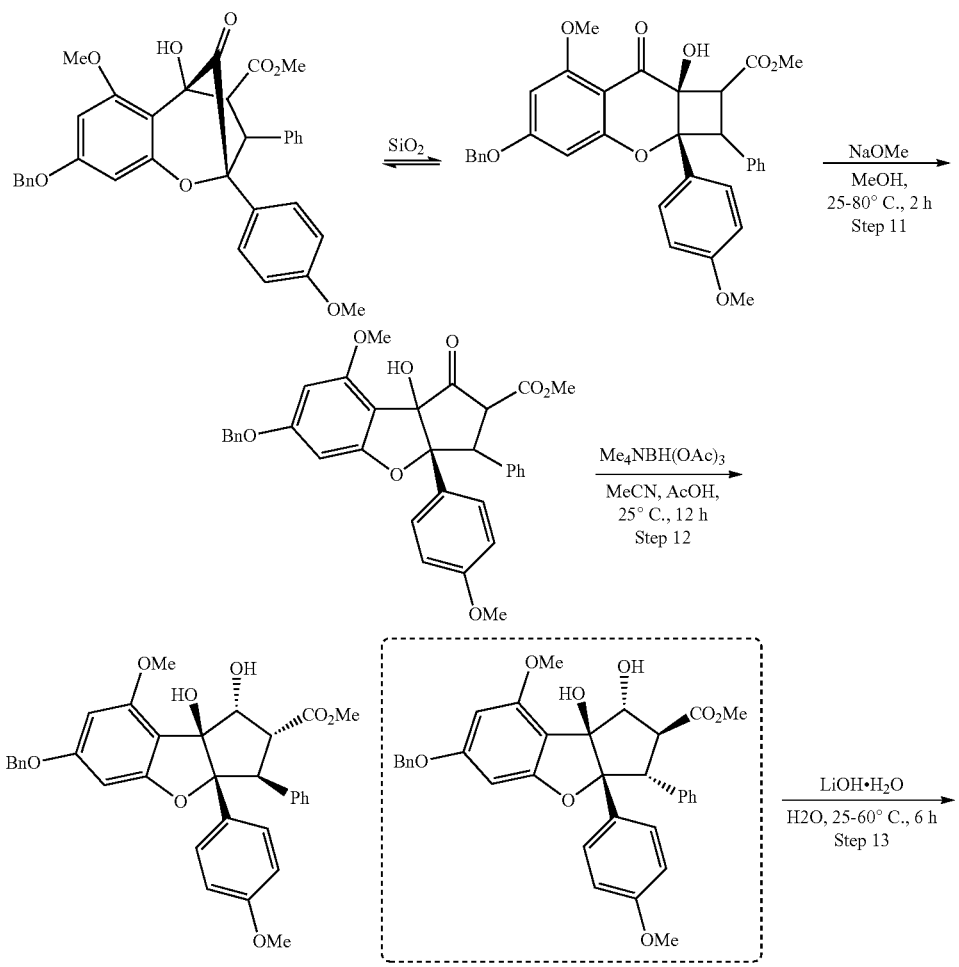
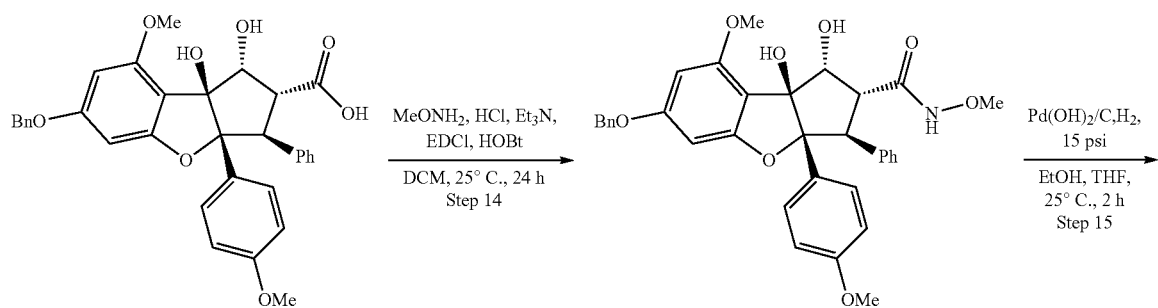

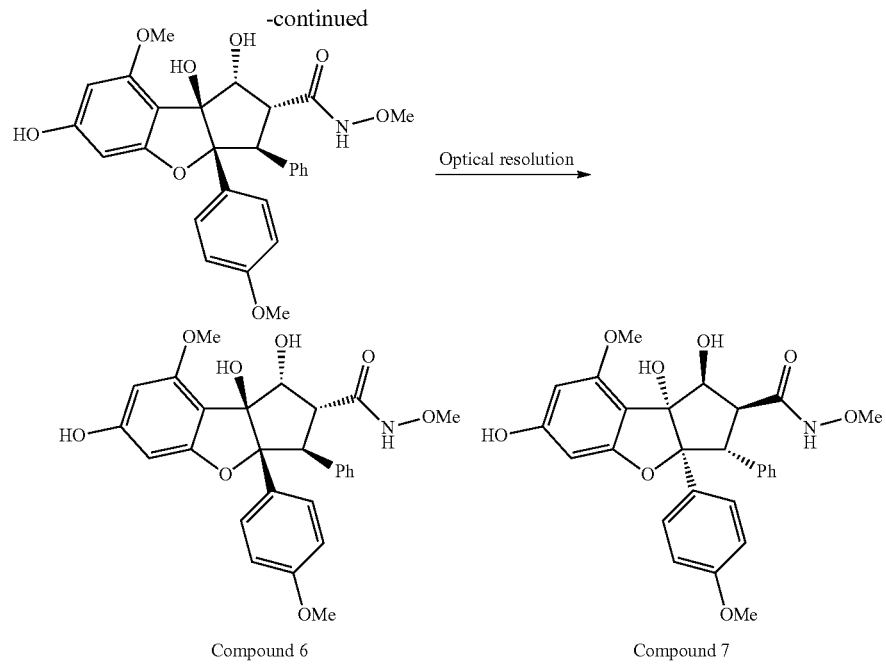

Compound 6          Compound 7

Step 1: 7-benzyloxy-5-methoxy-2-phenyl-chromen-4-one

A suspension of 5,7-dihydroxy-2-phenyl-chromen-4-one (25 g, 98.33 mmol, 1 eq) in acetone (300 mL) was treated with $K_2CO_3$ (40.77 g, 295.00 mmol, 3 eq) and bromomethylbenzene (16.82 g, 98.33 mmol, 11.68 mL, 1 eq). The mixture was heated to 60° C. and stirred for 12 h. And then it was cooled to 40° C., treated with dimethyl sulfate (37.00 g, 293.35 mmol, 27.82 mL, 2.98 eq), and stirred for 48 h at 40° C. The mixture was cooled to room temperature and the solid was removed by filtration. The cake was dissolved in water (1 L) and the solution was extracted with DCM (200 mL*3). The organic layer was combined with the filtrate that was previously concentrated to dryness under reduced pressure. The residue was washed with MTBE (100 mL*4) to give 7-benzyloxy-5-methoxy-2-phenyl-chromen-4-one (90% purity) (63 g, 90% purity, combined with another run of the same reaction) as light green solid.

LCMS: (M+H*): 359.0 @1.605 min (10-90% ACN in $H_2O$, 2.0 min).

$^1$H NMR: (400 MHz, $CDCl_3$) δ 7.92-7.83 (m, 2H), 7.59-7.33 (m, 8H), 6.69 (s, 1H), 6.67 (d, J=2.0 Hz, 1H), 6.47 (d, J=2.0 Hz, 1H), 5.17 (s, 2H), 3.96 (s, 3H).

Step 2: 1-(4-benzyloxy-2-hydroxy-6-methoxy-phenyl)ethanone 7-benzyloxy-5-methoxy-2-phenyl-chromen-4-one (48 g, 133.93 mmol, 1 eq) was added to a mixture of NaOH (375 g, 4.69 mol, 50% purity, 35 eq) and pyridine (211.68 g, 2.68 mol, 216 mL, 19.98 eq) at 25° C. The mixture was vigorously stirred and treated with diethylene glycol (284.48 g, 2.68 mol, 254 mL, 20.02 eq) at 25° C. Then the reaction mixture was heated to 100° C. and stirred for 12 h. After the reaction mixture was cooled to 25° C., it was acidified to pH=1 with 8 N aqueous hydrochloric acid solution. The aqueous portion was extracted with ethyl acetate (100 mL*4). The combined organic phase was washed with brine (200 mL), dried over $Na_2SO_4$, filtered and the filtrate was concentrated under reduced pressure. The residue was washed with ice methyl alcohol (20 mL*5). The collected solid was dried under reduced pressure to give 1-(4-benzyloxy-2-hydroxy-6-methoxy-phenyl)ethanone (31.5 g, with another run of the same reaction) as light yellow solid.

$^1$H NMR: (400 MHz, $CDCl_3$) δ 14.05 (s, 1H), 7.46-7.33 (m, 5H), 6.15 (d, J=2.2 Hz, 1H), 6.02 (d, J=2.2 Hz, 1H), 5.07 (s, 2H), 3.85 (s, 3H), 2.62 (s, 3H).

Step 3: 5-benzyloxy-2-[1-[tert-butyl(dimethyl)silyl]oxyvinyl]-3-methoxy-phenol A solution of 1-(4-benzyloxy-2-hydroxy-6-methoxy-phenyl)ethanone (26.5 g, 97.32 mmol, 1 eq) and TEA (24.62 g, 243.30 mmol, 33.86 mL, 2.5 eq) in DCM (300 mL) was cooled to 0° C. Then [tert-butyl(dimethyl)silyl]trifluoromethanesulfonate (51.45 g, 194.64 mmol, 44.74 mL, 2 eq) was added drop-wise to the mixture at 0° C. under $N_2$. After the addition, the reaction mixture was allowed to warm to 25° C. and stirred for 6 h. The reaction mixture was quenched with sat. aq $NaHCO_3$ (300 mL). The mixture was extracted with DCM (100 mL*2) and the separated organic layer was washed with brine (100 mL), dried over $Na_2SO_4$. After filtration, the filtrate was concentrated under reduced pressure to afford 5-benzyloxy-2-[1-[tert-butyl(dimethyl)silyl]oxyvinyl]-3-methoxy-phenol (60 g, crude) as brown oil. The crude product will be used directly in next step without further purification.

TLC Information: (PE/EtOAc=5/1)
Reactant: Rf=0.6
Product: Rf=0.8

Step 4: 5-benzyloxy-2-[2-[tert-butyl(dimethyl)silyl]oxyoxiran-2-yl]-3-methoxy-phenol To a mixture of 5-benzyloxy-2-[1-[tert-butyl(dimethyl)silyl]oxyvinyl]-3-methoxy-phenol (60 g, 155.22 mmol, 1 eq) and $NaHCO_3$ (32.60 g, 388.04 mmol, 15.09 mL, 2.5 eq)

in DCM (600 mL) was added m-CPBA (47.27 g, 232.83 mmol, 85% purity, 1.5 eq) in portions at 0° C. After the addition, the reaction mixture was stirred at 0° C. for 1 h, and then quenched by saturated aq. $Na_2SO_3$ (500 mL) and aq. $NaHCO_3$ (100 mL). Then the mixture was extracted with EtOAc (200 mL*4). The organic layer was washed with brine (300 mL), dried over $Na_2SO_4$, filtered and the filtrate was concentrated under reduced pressure to give 5-benzyloxy-2-[2-[tert-butyl(dimethyl)silyl]oxyoxiran-2-yl]-3-methoxy-phenol (66 g, crude) as brown oil. The crude product was used directly in next step without further purification.

TLC Information: (PE/EtOAc=10/1)
Reactant: Rf=0.5
Product: Rf=0.3

Step 5: 1-(4-benzyloxy-2-hydroxy-6-methoxy-phenyl)-2-hydroxy-ethanone

To a solution of 5-benzyloxy-2-[2-[tert-butyl(dimethyl)silyl]oxyoxiran-2-yl]-3-methoxy-phenol (66 g, 163.95 mmol, 1 eq) in THF (600 mL) and $H_2O$ (60 mL) was added 4-methylbenzenesulfonic acid hydrate (3.12 g, 16.41 mmol, 0.1 eq) at 25° C. The mixture was stirred for 80° C. at 6 hours. The reaction mixture was quenched with saturated aqueous sodium bicarbonate solution (500 mL) and concentrated under reduced pressure to remove THF. Then the residue aqueous phase was extracted with EtOAc (150 mL*4). The organic phase was washed with brine (300 mL), dried over Na2SO4, filtered and the filtrate was concentrated under reduced pressure. The residue solid was washed with EtOH (40 mL*4). The collected solid was dried under reduced pressure to give 1-(4-benzyloxy-2-hydroxy-6-methoxy-phenyl)-2-hydroxy-ethanone (91.29% purity) (18 g, combined with another run of the same reaction) as gray solid.

LCMS: (M+H+): 289.2 @1.170 min (5-95% ACN in $H_2O$, 2.0 min).
$^1$H NMR: (400 MHz, $CDCl_3$) δ 13.22 (s, 1H), 7.46-7.32 (m, 5H), 6.20 (d, J=2.4 Hz, 1H), 6.03 (d, J=2.2 Hz, 1H), 5.09 (s, 2H), 4.72 (d, J=4.6 Hz, 2H), 3.86 (s, 3H), 3.77 (br s, 1H).

Step 6: [2-[4-benzyloxy-2-methoxy-6-(4-methoxybenzoyl)oxy-phenyl]-2-oxo-ethyl]4-methoxybenzoate A solution of 1-(4-benzyloxy-2-hydroxy-6-methoxy-phenyl)-2-hydroxy-ethanone (7 g, 24.28 mmol, 1 eq) in DCM (100 mL) was treated with DMAP (149 mg, 1.22 mmol, 5.02e-2 eq) and TEA (7.4 g, 73.13 mmol, 10.18 mL, 3.01 eq). The mixture was cooled to 0° C., treated with 4-methoxybenzoyl chloride (8.3 g, 48.65 mmol, 6.69 mL, 2 eq) dropwise. After the addition, the mixture was allowed to warm to 25° C. and stirred for 3 h. The reaction mixture was quenched with 1 N aqueous hydrochloric acid (100 mL), and the organic layer was separated. The aqueous phase was back-extracted with DCM (40 mL*3). The combined organic phases were washed with brine (100 mL), dried over $Na_2SO_4$, filtered and the filtrate was concentrated under reduced pressure. The residue was washed with EtOH (20 mL*3). The collected solid was dried under recued pressure to give [2-[4-benzyloxy-2-methoxy-6-(4-methoxybenzoyl)oxy-phenyl]-2-oxo-ethyl]4-methoxybenzoate (25 g, 44.92 mmol, 92.50% yield) as white solid.

$^1$H NMR: (400 MHz, $CDCl_3$) δ 8.14-8.09 (m, 2H), 8.00-7.96 (m, 2H), 7.45-7.36 (m, 5H), 6.97-6.92 (m, 2H), 6.91-6.87 (m, 2H), 6.56 (d, J=2.1 Hz, 1H), 6.48 (d, J=2.2 Hz, 1H), 5.25 (s, 2H), 5.08 (s, 2H), 3.86 (s, 3H), 3.84 (d, J=2.0 Hz, 6H).

Step 7: [1-(4-benzyloxy-2-hydroxy-6-methoxy-benzoyl)-2-(4-methoxyphenyl)-2-oxo-ethyl]4-methoxybenzoate A stirred solution of [2-[4-benzyloxy-2-methoxy-6-(4-methoxybenzoyl)oxy-phenyl]-2-oxo-ethyl]4-methoxybenzoate (25 g, 44.92 mmol, 1 eq) in THF (300 mL) was cooled to −70° C. and was treated with LiHMDS (1 M, 135 mL, 3.01 eq) dropwise. The mixture was allowed to warm to 25° C. and stirred for 3 h. The mixture was poured into saturated aqueous NH4Cl solution (400 mL). The aqueous phase was extracted with ethyl acetate (100 mL*3). The combined organic phases were washed with brine (100 mL), dried over Na2SO4, filtered and concentrated in vacuum to give [1-(4-benzyloxy-2-hydroxy-6-methoxy-benzoyl)-2-(4-methoxyphenyl)-2-oxo-ethyl]4-methoxybenzoate (25 g, crude) as gray solid. The crude product will be used directly in next step without further purification.

$^1$H NMR: (400 MHz, $CDCl_3$) δ 13.30 (s, 1H), 8.10-8.06 (m, 2H), 8.04-7.99 (m, 2H), 7.43-7.37 (m, 6H), 7.00-6.97 (m, 2H), 6.94-6.90 (m, 2H), 6.20 (d, J=2.2 Hz, 1H), 5.92 (d, J=2.2 Hz, 1H), 5.06 (s, 2H), 3.88 (s, 3H), 3.85 (s, 3H), 3.34 (s, 3H).

Step 8: [7-benzyloxy-5-methoxy-2-(4-methoxyphenyl)-4-oxo-chromen-3-yl]4-methoxybenzoate To a suspension of [1-(4-benzyloxy-2-hydroxy-6-methoxy-benzoyl)-2-(4-methoxyphenyl)-2-oxo-ethyl]4-methoxybenzoate (25 g, 44.92 mmol, 1 eq) in AcOH (300 mL) was added $H_2SO_4$ (22.08 g, 225.13 mmol, 12 mL, 5.01 eq) at 25° C. Then the mixture was stirred at 25° C. for 12 h. The reaction mixture was quenched with cooled water (400 mL) and stirred for 10 min. It was filtered. The filter cake was washed with EtOH (30 mL*5). Then the filter cake was collected and dried under reduced pressure to give [7-benzyloxy-5-methoxy-2-(4-methoxyphenyl)-4-oxo-chromen-3-yl]4-methoxybenzoate (18 g, 33.42 mmol, 74.41% yield) as light yellow solid. The crude product was used directly in next step without further purification.

LCMS: (M+H+): 539.1 @1.683 min (10-90% ACN in $H_2O$, 2.0 min).
$^1$H NMR: (400 MHz, $CDCl_3$) δ 8.20-8.14 (m, 2H), 7.91-7.85 (m, 2H), 7.50-7.36 (m, 5H), 6.99-6.92 (m, 4H), 6.64 (d, J=2.2 Hz, 1H), 6.45 (d, J=2.2 Hz, 1H), 5.16 (s, 2H), 3.91 (s, 3H), 3.89 (s, 3H), 3.83 (s, 3H).

Step 9: 7-benzyloxy-3-hydroxy-5-methoxy-2-(4-methoxyphenyl)chromen-4-one

A suspension of [7-benzyloxy-5-methoxy-2-(4-methoxyphenyl)-4-oxo-chromen-3-yl]4-methoxybenzoate (18 g, 33.42 mmol, 1 eq) in EtOH (200 mL) was treated with NaOH (53.48 g, 66.85 mmol, 5% purity, 2 eq). The suspension was heated to 80° C. and stirred for 6 h. The reaction mixture was diluted with water (100 mL) and the solution was acidified to pH=5 with aq. HCl (2 N). Then the mixture was filtered and the filter cake was washed with EtOH (20 mL*5). The filter cake was collected and dried under vacuum to give the crude product. The residue was purified by column chromatography ($SiO_2$, DCM/Ethyl acetate=10/1 to 5/1) to give 7-benzyloxy-3-hydroxy-5-methoxy-2-(4-methoxyphenyl)chromen-4-one (11 g, 27.20 mmol, 81.38% yield) as yellow solid.

LCMS: (M+H+): 405.2 @1.427 min (10-90% ACN in H$_2$O, 2.0 min).

$^1$H NMR: (400 MHz, CDCl$_3$) δ 8.17 (d, J=8.3 Hz, 2H), 7.52-7.34 (m, 6H), 7.03 (d, J=8.3 Hz, 2H), 6.63 (br s, 1H), 6.43 (s, 1H), 5.15 (s, 2H), 3.97 (s, 3H), 3.89 (s, 3H).

Step 10

A solution of 7-benzyloxy-3-hydroxy-5-methoxy-2-(4-methoxyphenyl)chromen-4-one (5 g, 12.36 mmol, 1 eq) and methyl (E)-3-phenylprop-2-enoate (23.06 g, 142.18 mmol, 11.5 eq) in DCM (500 mL), MeOH (200 mL), and MeCN (200 mL) was placed in a jacketed flask. Then the stirring mixture was cooled to 3° C. and irradiated (mercury lamp radiation (400 W)) under N$_2$ for 11 days. The reaction mixture was poured into ice water (500 mL) and the organic phases were separated. The aqueous phase was back extracted with DCM (200 mL*3). The organic layer was washed with brine (600 mL), dried over Na$_2$SO$_4$, filtered and the filtrate was concentrated under reduced pressure. The residue was purified by column chromatography (SiO$_2$, Petroleum ether/Ethyl acetate=10/1 to 5/1 to 1/1) to give the desired product (5.5 g, crude) as orange solid which was used in the next step directly.

Step 11

To a stirred solution of NaOMe (4.77 g, 26.47 mmol, 30% purity, 3 eq) in MeOH (10 mL) was added a solution of the product of Step 10 (5.00 g, 8.82 mmol, 1 eq) in MeOH (30 mL) at 25° C. Then the mixture was stirred at 80° C. for 2 h. The reaction mixture was filtered and the filter cake was washed with MeOH (5 mL*4). The collected solid was re-dissolved in saturated aq. NH4C$_1$ solution (50 mL) and the solution was extracted with EtOAc (20 mL*4). The organic layer was washed with brine (40 mL), dried over Na$_2$SO$_4$, filtered and the filtrate was concentrated under reduced pressure. Desired product (2.1 g, 3.19 mmol, 36.12% yield, 86% purity) was obtained as light yellow solid. The crude product was used directly in next step without further purification. Due to the tautomerism of the structure, two peaks were detected on LCMS.

LCMS: (M-17): 549.3@1.277 min (5-95% ACN in H$_2$O, 2.0 min).

Step 12: Methyl 6-benzyloxy-1,8b-dihydroxy-8-methoxy-3a-(4-methoxyphenyl)-3-phenyl-2,3-dihydro-1H-cyclopenta[b]benzofuran-2-carboxylate To a stirred solution of starting material (2.10 g, 3.71 mmol, 1 eq) and AcOH (2.23 g, 37.07 mmol, 2.12 mL, 10 eq) in MeCN (30 mL) was added tetramethylammonium; triacetoxyboranuide (5.85 g, 22.24 mmol, 6 eq). Then the mixture was stirred at 25° C. for 12 h. The reaction mixture was poured into ice-water (60 mL). The aqueous phase was extracted with ethyl acetate (30 mL*4). The combined organic phases were washed with brine (50 mL), dried over anhydrous Na$_2$SO$_4$, filtered and concentrated in vacuum to give methyl 6-benzyloxy-1,8b-dihydroxy-8-methoxy-3a-(4-methoxyphenyl)-3-phenyl-2,3-dihydro-1H-cyclopenta[b]benzofuran-2-carboxylate (1.7 g, crude) as light yellow solid. The crude product was used directly in next step without further purification.

LCMS: (M-17): 551.3, (M+23): 591.2@1.240 min, (5-95% ACN in H$_2$O, 2.0 min).

Step 13: 6-benzyloxy-1,8b-dihydroxy-8-methoxy-3a-(4-methoxyphenyl)-3-phenyl-2,3-dihydro-1H-cyclopenta[b]benzofuran-2-carboxylic acid To a solution of the methyl 6-benzyloxy-1,8b-dihydroxy-8-methoxy-3a-(4-methoxyphenyl)-3-phenyl-2,3-dihydro-1Hcyclopenta[b]benzofuran-2-carboxylate (1.70 g, 2.99 mmol, 1 eq) in THF (20 mL) and H$_2$O (5 mL) was added LiOH·H$_2$O (503.00 mg, 11.99 mmol, 4.01 eq) at 25° C. The solution was stirred at 60° C. for 6 hours. The reaction mixture was diluted with water (50 mL). The solution was adjusted to pH=3 with aq HCl (2 N). Then the solution was extracted with EtOAc (20 mL*3). The combined organic layer was washed with brine (30 mL), dried over Na$_2$SO$_4$, filtered and the filtrated was concentrated under reduced pressure to afford 6-benzyloxy-1,8b-dihydroxy-8-methoxy-3a-(4-methoxyphenyl)-3-phenyl-2,3-dihydro-1H-cyclopenta[b]benzofuran-2-carboxylic acid (1.7 g, crude) as light yellow solid.

LCMS: (M-17): 537.3@1.218 min (5-95% ACN in H$_2$O, 2.0 min).

SFC: (Retention time: 3.54; 3.72; 4.03; 4.28).

Step 14: 6-benzyloxy-1,8b-dihydroxy-N,8-dimethoxy-3a-(4-methoxyphenyl)-3-phenyl-2,3-dihydro-1H-cyclopenta[b]benzofuran-2-carboxamide To a solution of 6-benzyloxy-1,8b-dihydroxy-8-methoxy-3a-(4-methoxyphenyl)-3-phenyl-2,3-dihydro-1Hcyclopenta[b]benzofuran-2-carboxylic acid (1.70 g, 3.07 mmol, 1 eq), O-methyl hydroxylamine; hydrochloride (768.02 mg, 9.20 mmol, 698.20 uL, 3 eq) in DCM (30 mL) was added HOBt (620.98 mg, 4.60 mmol, 1.5 eq), EDCI (705.99 mg, 3.68 mmol, 1.2 eq) and TEA (1.40 g, 13.81 mmol, 1.92 mL, 4.5 eq) at 25° C. Then the mixture was stirred at 25° C. for 24 h. The reaction mixture was diluted with water (100 mL). The solution was extracted with DCM (40 mL*4). The organic layer was washed with brine (50 mL), dried over Na$_2$SO$_4$, filtered and the filtrate was concentrated under reduced pressure. The residue was purified by column chromatography (SiO$_2$, Petroleum ether/Ethyl acetate=1/1 to 1/4) to give 6-benzyloxy-1,8b-dihydroxy-N,8-dimethoxy-3a-(4-methoxyphenyl)-3-phenyl-2,3-dihydro-1H-cyclopenta[b]benzofuran-2-carboxamide (410 mg, 702.50 μmol, 22.92% yield) as light yellow solid.

Step 15: (1R,2R,3S,3aR,8bS)-1,6,8b-trihydroxy-N,8-dimethoxy-3a-(4-methoxyphenyl)-3-phenyl-2,3-dihydro-1H-cyclopenta[b]benzofuran-2-carboxamide and (1S,2S,3R,3aS,8bR)-1,6,8b-trihydroxy-N,8-dimethoxy-3a-(4-methoxyphenyl)-3-phenyl-2,3,3a,8b-tetrahydro-1H-cyclopenta[b]benzofuran-2-carboxamide To a solution of 6-benzyloxy-1,8b-dihydroxy-N,8-dimethoxy-3a-(4-methoxyphenyl)-3-phenyl-2,3-dihydro-1Hcyclopenta[b]benzofuran-2-carboxamide (410.00 mg, 702.50 μmol, 1 eq) in EtOH (5 mL) and EtOAc (5 mL) was added Pd(OH)$_2$/C (0.2 g, 20% purity) under N2. The suspension was degassed under vacuum and purged with H2 three times. The mixture was stirred under H$_2$ (15 psi) at 25° C. for 2 hours. The reaction mixture was filtered through a pad of Celite and the filter cake was washed with EtOAc (10 mL×5). The filtrate was concentrated under reduced pressure to afford the crude product. The residue was purified by neutral prep-HPLC (column: Waters Xbridge 150*25 5u; mobile phase: [water (10 mM $NH_4HCO_3$)-ACN]; B %: 15%-35%, 11 min). The purified product was checked by chiral SFC (Retention time: P1: 2.71 min; P2: 3.85 min), and each isomer was separated by chiral SFC to give P1 and P2.

Compound 6:

(1R,2R,3S,3aR,8bS)-1,6,8b-trihydroxy-N,8-dimethoxy-3a-(4-methoxyphenyl)-3-phenyl-2,3-dihydro-1Hcyclopenta[b]benzofuran-2-carboxamide (75.6 mg, 153.19 μmol, 21.81% yield, 100% purity: 100% ee) as white solid.

LCMS: (M+H+): 494.0@2.278 min (10-80% ACN in $H_2O$, 4.5 min)

$^1$H NMR: (400 MHz, METHANOL-d4) δ7.33 (d, J=8.9 Hz, 2H), 7.15-7.11 (m, 3H), 6.98 (dd, J=3.5, 5.9 Hz, 2H), 6.88 (d, J=8.9 Hz, 2H), 6.05 (d, J=1.7 Hz, 1H), 5.99 (d, J=1.8 Hz, 1H), 4.65 (d, J=10.3 Hz, 1H), 3.96 (d, J=12.6 Hz, 1H), 3.77 (d, J=2.1 Hz, 6H), 3.43 (s, 3H), 2.82 (dd, J=10.3, 12.6 Hz, 1H).

SFC: (Retention time: 2.61; % ee: 100%).

Optical rotation: (−37.43°±1.65°; c=0.5 g/100 mL diluted with methanol, 20° C.).

Compound 7:

(1S,2S,3R,3aS,8bR)-1,6,8b-trihydroxy-N,8-dimethoxy-3a-(4-methoxyphenyl)-3-phenyl-2,3,3a,8b-tetrahydro-1H-cyclopenta[b]benzofuran-2-carboxamide (74.1 mg, 149.76 μmol, 21.32% yield, 99.74% purity, % ee: 100%) obtained as white solid.

LCMS: (M+H): 494.0@2.277 min (10-80% ACN in $H_2O$, 4.5 min).

$^1$H NMR: (400 MHz, METHANOL-d4) δ 7.34 (d, J=8.9 Hz, 2H), 7.17-7.12 (m, 3H), 6.99 (dd, J=3.4, 6.0 Hz, 2H), 6.88 (d, J=8.9 Hz, 2H), 6.05 (d, J=1.7 Hz, 1H), 5.99 (d, J=1.8 Hz, 1H), 4.66 (d, J=10.4 Hz, 1H), 3.97 (d, J=12.7 Hz, 1H), 3.78 (d, J=1.2 Hz, 6H), 3.44 (s, 3H), 2.82 (dd, J=10.3, 12.7 Hz, 1H).

SFC: (Retention time: 3.73; 100% ee).

Optical rotation: (33.14°±3.37°; c=0.5 g/100 mL diluted with methanol, 20° C.).

Example 4. Synthesis of (1S,2S,3R,3aS,8bR)-1,8b-dihydroxy-3a-(4-hydroxyphenyl)-6,8-dimethoxy-3-phenyl-2,3-dihydro-1H-cyclopenta[b]benzofuran-2-carboxamide (Compound 8) and (1R,2R,3S,3aR,8bS)-1,8b-dihydroxy-3a-(4-hydroxyphenyl)-6,8-dimethoxy-3-phenyl-2,3-dihydro-1H-cyclopenta[b]benzofuran-2-carboxamide (Compound 9)

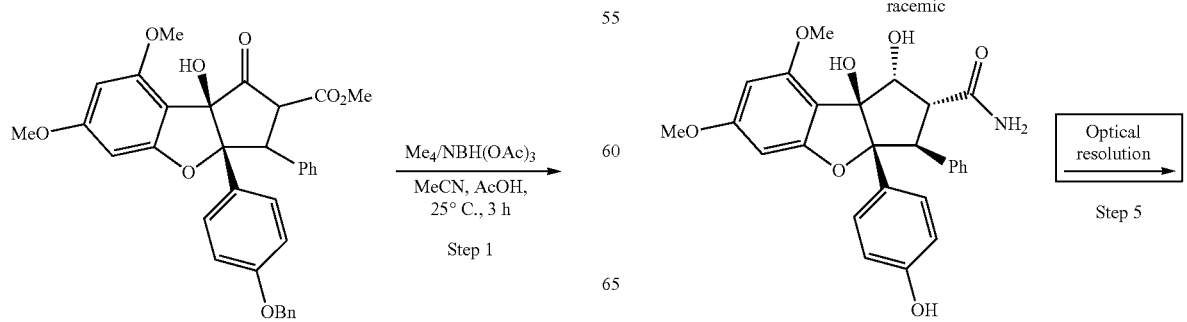

-continued

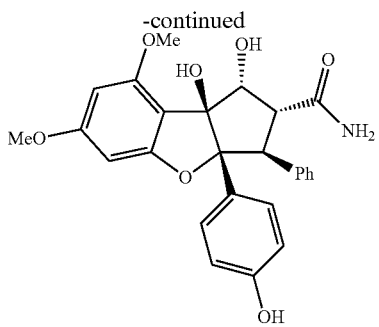

Compound 8

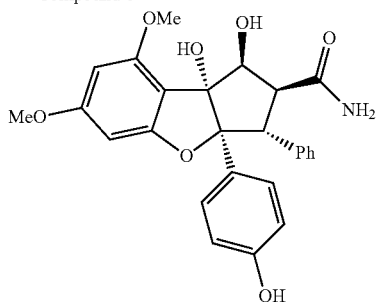

Compound 9

Step 1: Methyl (1R,3aR,8bS)-3a-(4-benzyloxyphenyl)-1,8b-dihydroxy-6,8-dimethoxy-3-phenyl-2,3-dihydro-1H-cyclopenta[b]benzofuran-2-carboxylate To a stirred solution of methyl (3aR,8bR)-3a-(4-benzyloxyphenyl)-8b-hydroxy-6,8-dimethoxy-1-oxo-3-phenyl-2,3-dihydrocyclopenta[b]benzofuran-2-carboxylate (2.6 g, 4.59 mmol, 1 eq) and AcOH (2.76 g, 45.89 mmol, 2.62 mL, 10 eq) in MeCN (30 mL) was added tetramethylammonium triacetoxyborohydride (7.24 g, 27.53 mmol, 6 eq). Then the mixture was stirred at 25° C. for 3 h, and then was poured into ice-water (50 mL). The aqueous phase was extracted with ethyl acetate (20 mL*4). The combined organic phases were washed with brine (20 mL), dried over anhydrous $Na_2SO_4$, filtered and concentrated in vacuum to give methyl (1R,3aR,8bS)-3a-(4-benzyloxyphenyl)-1,8b-dihydroxy-6,8-dimethoxy-3-phenyl-2,3-dihydro-1H-cyclopenta[b]benzofuran-2-carboxylate (2.6 g, crude) as light yellow solid. The crude product was used directly in next step without further purification.

LCMS: (M-17): 551.1 and (M+Na+): 591.1@1.277 min (5-95% ACN in $H_2O$, 2.0 min).

Step 2: (1R,3aR,8bS)-3a-(4-benzyloxyphenyl)-1,8b-dihydroxy-6,8-dimethoxy-3-phenyl-2,3-dihydro-1H-cyclopenta[b]benzofuran-2-carboxylic acid To a solution of the methyl (1R,3aR,8bS)-3a-(4-benzyloxyphenyl)-1,8b-dihydroxy-6,8-dimethoxy-3-phenyl-2,3-dihydro-1H-cyclopenta[b]benzofuran-2-carboxylate (2.6 g, 4.57 mmol, 1 eq) in THF (28 mL) and $H_2O$ (7 mL) was added LiOH·$H_2O$ (767.00 mg, 18.28 mmol, 4.00 eq) at 25° C. The solution was stirred at 60° C. for 12 hours. The reaction mixture was diluted with water (50 mL). The solution was adjusted to pH=3 with aq HCl (2 N). Then the result solution was extracted with EtOAc (20 mL*5). The combined organic layer was washed with brine (40 mL), dried over $Na_2SO_4$, filtered and the filtrate was concentrated under reduced pressure to afford (1R,3aR,8bS)-3a-(4-benzyloxyphenyl)-1,8b-dihydroxy-6,8-dimethoxy-3-phenyl-2,3-dihydro-1H-cyclopenta[b]benzofuran-2-carboxylic acid (2.5 g, crude) as light yellow solid. The crude product was used directly in next step without further purification.

LCMS: (M-17): 537.4 @1.216 min (5-95% ACN in $H_2O$, 2.0 min).

Step 3: (1R,3aR,8bS)-3a-(4-benzyloxyphenyl)-1,8b-dihydroxy-N,6,8-trimethoxy-3-phenyl-2,3-dihydro-1H-cyclopenta[b]benzofuran-2-carboxamide To a solution of (1R,3aR,8bS)-3a-(4-benzyloxyphenyl)-1,8b-dihydroxy-6,8-dimethoxy-3-phenyl-2,3-dihydro-1H-cyclopenta[b]benzofuran-2-carboxylic acid (2.5 g, 4.51 mmol, 1 eq), O-methylhydroxylamine hydrochloride (1.13 g, 13.51 mmol, 1.03 mL, 3.00 eq) in DCM (30 mL) was added HOBt (914.29 mg, 6.77 mmol, 1.5 eq), EDCI (1.04 g, 5.40 mmol, 1.2 eq) and TEA (2.05 g, 20.26 mmol, 2.82 mL, 4.49 eq) at 25° C. under nitrogen. Then the mixture was stirred at 25° C. for 12 h. The reaction mixture was diluted with water (50 mL). The solution was extracted with DCM (20 mL*4). The organic layer was washed with brine (30 mL), dried over $Na_2SO_4$, filtered and the filtrate was concentrated under reduced pressure. The residue was purified by column chromatography ($SiO_2$, Petroleum ether/Ethyl acetate=1/1 to 1/4) to give (1R,3aR,8bS)-3a-(4-benzyloxyphenyl)-1,8b-dihydroxy-N,6,8-trimethoxy-3-phenyl-2,3-dihydro-1H-cyclopenta[b]benzofuran-2-carboxamide (1.9 g, 3.21 mmol, 71.29% yield, 98.72% purity) as white solid.

LCMS: (M+H+): 584.3 @1.153 min (5-95% ACN in $H_2O$, 2.0 min).

HPLC: @3.532 min (10-80% ACN in $H_2O$, 5.2 min).

Chiral SFC: Retention time: (Peak 1:3.50; Peak 2: 3.67).

Step 4: 1,8b-dihydroxy-3a-(4-hydroxyphenyl)-N,6,8-trimethoxy-3-phenyl-2,3-dihydro-1H-cyclopenta[b]benzofuran-2-carboxamide To a solution of (1R,3aR,8bS)-3a-(4-benzyloxyphenyl)-1,8b-dihydroxy-N,6,8-trimethoxy-3-phenyl-2,3-dihydro-1H-cyclopenta[b]benzofuran-2-carboxamide (0.6 g, 1.03 mmol, 1 eq) in EtOH (5 mL) and THF (5 mL) was added Pd(OH)$_2$/C (1.03 mmol, 20% purity) under $N_2$. The suspension was degassed under vacuum and purged with H2 three times. The mixture was stirred under $H_2$ (15 psi) at 25° C. for 5 h. The reaction mixture was filtered through a pad of Celite and the filter cake was washed with THF (10 mL*4) and EtOH (10 mL*4). The filtrate was concentrated under reduced pressure to afford the crude product. The residue was purified by prep-TLC (Methanol/Ethyl acetate=20/1) to afford the two products (product 1: 180 mg; product 2: 280 mg). Each product was further purified by neutral prep-HPLC (product 1: column: Agela Durashell C18 150*25 5u; mobile phase: [water (10 mM NH4HCO$_3$)-ACN]; B %: 25%-%, 10 min; product 2: column: Agela DurashellC18 150*25 5u; mobile phase: [water (10 mM NH$_4$HCO$_3$)-ACN]; B %: 23%-53%, 10 min) to afford the purified products.

Product 1:
1,8b-dihydroxy-3a-(4-hydroxyphenyl)-N,6,8-trimethoxy-3-phenyl-2,3-dihydro-1H-cyclopenta[b]benzofuran-2-carboxamide (130 mg crude, 15 mg pure) as white solid.

LCMS: (M+H+): 494.1 @2.313 min (10-80% ACN in $H_2O$, 4.5 min).

¹H NMR: (400 MHz, DMSO-d6) δ 11.12 (br s, 1H), 9.03 (s, 1H), 7.08-7.02 (m, 2H), 7.01-6.95 (m, 1H), 6.92-6.85 (m, 4H), 6.42 (d, J=8.7 Hz, 2H), 6.27 (d, J=1.7 Hz, 1H), 6.12 (d, J=1.7 Hz, 1H), 4.96 (s, 1H), 4.62 (d, J=3.3 Hz, 1H), 4.56 (br s, 1H), 4.14 (d, J=14.2 Hz, 1H), 3.78 (s, 3H), 3.75 (s, 3H), 3.55 (dd, J=5.5, 14.2 Hz, 1H), 3.49 (s, 3H).

Product 2:

1,8b-dihydroxy-3a-(4-hydroxyphenyl)-6,8-dimethoxy-3-phenyl-2,3-dihydro-1H-cyclopenta[b]benzofuran-2-carboxamide (115.3 mg, 248.77 μmol, 24.20% yield, 100% purity) as white solid.

LCMS: (M+H+): 464.1 @2.235 min (10-80% ACN in $H_2O$, 4.5 min). ¹H NMR: (400 MHz, DMSO-d6) δ 8.98 (s, 1H), 7.63 (br s, 1H), 7.07-7.00 (m, 2H), 6.99-6.88 (m, 5H), 6.40 (d, J=8.4 Hz, 2H), 6.24 (s, 1H), 6.09 (s, 1H), 4.88 (s, 1H), 4.61 (d, J=3.1 Hz, 1H), 4.57-4.52 (m, 1H), 4.11 (d, J=14.1 Hz, 1H), 3.77 (s, 3H), 3.73 (s, 3H).

Step 5: (1R,2R,3S,3aR,8bS)-1,8b-dihydroxy-3a-(4-hydroxyphenyl)-6,8-dimethoxy-3-phenyl-2,3-dihydro-1H-cyclopenta[b]benzofuran-2-carboxamide (Compound 8) and (1S,2S,3R,3aS,8bR)-1,8b-dihydroxy-3a-(4-hydroxyphenyl)-6,8-dimethoxy-3-phenyl-2,3-dihydro-1H-cyclopenta[b]benzofuran-2-carboxamide (Compound 9)

Separation of the enantiomers of Product 2 from the previous step: Step 5a: Chiral SFC (Instrument: Thar SFC80 preparative SFC; Column: Chiralcel OJ-H 250*30 mm i.d. 5u; Mobile phase: A for $CO_2$ and B for MeOH (0.1% $NH_3H_2O$); Gradient: B %=30%; Flow rate: 65 g/min; Wavelength: 220 nm; Column temperature: 40° C.; System back pressure: 100 bar) gave compound 9 (Rt: 2.766 min, 18 mg), partially separated compound 8 (Rt: 3.040 min, 15 mg), and 20 mg mixture of compound 8 and compound 9.

Step 5b: Partially separated compound 8 from step 5a was further separated by SFC (Instrument: Thar SFC80 preparative SFC; Column: Chiralpak IC-H 250*30 mm i.d. 5u; Mobile phase: A for $CO_2$ and B for EtOH (0.1% $NH_3H_2O$); Gradient: B %=42%; Flow rate: 70 g/min; Wavelength: 220 nm; Column temperature: 40° C.; System back pressure: 100 bar) again to give Compound 9 (Rt: 2.766 min, 2 mg), and Compound 8 (Rt: 3.040 min, 7 mg).

Step 5c: The 20 mg mixture of Compound 9 and Compound 8 from step 5a was separated by SFC (Instrument: Thar SFC80 preparative SFC; Column: Chiralpak IC-H 250*30 mm i.d. 5u; Mobile phase: A for $CO_2$ and B for EtOH (0.1% $NH_3H_2O$); Gradient: B %=42%; Flow rate: 70 g/min; Wavelength: 220 nm; Column temperature: 40° C.; System back pressure: 100 bar) again to give purified compound 9 (Rt: 2.766 min, 6.5 mg) and compound 8 (Rt: 3.040 min, 3.1 mg).

A total of 26.5 mg of Compound 9 and 25.1 mg Compound 8 was obtained.

Compound 8:

(1R,2R,3S,3aR,8bS)-1,8b-dihydroxy-3a-(4-hydroxyphenyl)-6,8-dimethoxy-3-phenyl-2,3-dihydro-1H-cyclopenta[b]benzofuran-2-carboxamide (25.1 mg, 54.16 μmol, 27.9% yield) was obtained as white solid.

LCMS: (M+H+): 464.0 @2.215 min (10-80% ACN in $H_2O$, 4.5 min).

¹H NMR: (400 MHz, ACETONITRILE-d3) δ 7.14-6.98 (m, 8H), 6.84 (s, 1H), 6.53 (d, J=8.7 Hz, 2H), 6.47 (br s, 1H), 6.26 (d, J=1.8 Hz, 1H), 6.16 (d, J=1.8 Hz, 1H), 5.79 (br s, 1H), 4.68 (d, J=4.0 Hz, 1H), 4.21 (d, J=14.2 Hz, 1H), 3.88-3.79 (m, 9H), 3.05 (s, 1H).

Chiral SFC: (Retention time: 3.04; 100% ee).

Optical rotation: (−71.88°±13.08°; c=0.5 g/100 mL diluted with methanol, 20° C.).

Compound 9:

(1S,2S,3R,3aS,8bR)-1,8b-dihydroxy-3a-(4-hydroxyphenyl)-6,8-dimethoxy-3-phenyl-2,3-dihydro-1H-cyclopenta[b]benzofuran-2-carboxamide (26.5 mg, 57.2 μmol, 27.9% yield) was obtained as white solid.

LCMS: (M+H+): 464.0 @2.215 min (10-80% ACN in $H_2O$, 4.5 min).

¹H NMR: (400 MHz, ACETONITRILE-d3) δ 7.14-7.00 (m, 8H), 6.84 (br s, 1H), 6.53 (d, J=8.7 Hz, 2H), 6.47 (br s, 1H), 6.26 (d, J=1.8 Hz, 1H), 6.17 (d, J=2.0 Hz, 1H), 5.78 (br s, 1H), 4.69 (d, J=5.6 Hz, 1H), 4.21 (d, J=14.2 Hz, 1H), 3.89-3.78 (m, 9H), 3.06 (br s, 1H).

Chiral SFC: (Retention time: 2.766; 98.6% ee).

Optical rotation: (66.27°±8.51°; 0.5 g/100 mL diluted with methanol, 20° C.).

Example 5. Evaluation of Biological Activity In Vitro

The biological activity of compounds of the invention was evaluated in several assays. In a cell viability assay using cancer and normal cells lines MOLT-4 (human acute lymphoblastic leukemia [ALL]) and MRC-5 (human lung fibroblast), respectively, cell viability was assessed after 72 hours of exposure to a range of concentrations, using cell titer glow reagent from Promega to assess viability. Compound 1 killed T-ALL cells with an $IC_{50}$ of 5.3 nM, whereas the $IC_{50}$ was >1000 nM against non-cancer cells.

In a cell viability assay using KOPTK1 cells, a murine T-cell ALL cell line, Compound 1 had an $IC_{50}$ of 50 nM, and a racemic mixture of Compounds 8 and 9, 10 nM.

FIGS. 1A, 1B, 1C, and 1D show the activity of compounds of the invention, compared to (−)-CR31B and (+)-CR31B in cell viability assays using (A) DHL6 cells, (B) Jurkat cells, (C) DoHH2 cells, and (D) LY8 cells. FIG. 2 shows the activity using DHL8 cells. The following table reports the $IC_{50}$s (in nM) for each lymphoma and leukemia cell type.

| Cell viability $IC_{50}$ (nM) Cell type: | (−)-CR31B | (+)-CR31B | Compound 1 | Racemic mixture of Compounds 8 and 9 |
|---|---|---|---|---|
| DHL6 | 7.621 | ~4295 | 51.52 | 947.1 |
| Jurkat | 6.419 | ~3111 | 62.97 | 1726 |
| DoHH2 | 7.297 | 2532 | 36.72 | 987.3 |
| LY8 | 5.927 | 16465 | 38.93 | 2913 |
| DHL8 | 7.211 | 7478 | 74.94 | 1041 |

Figure 3:
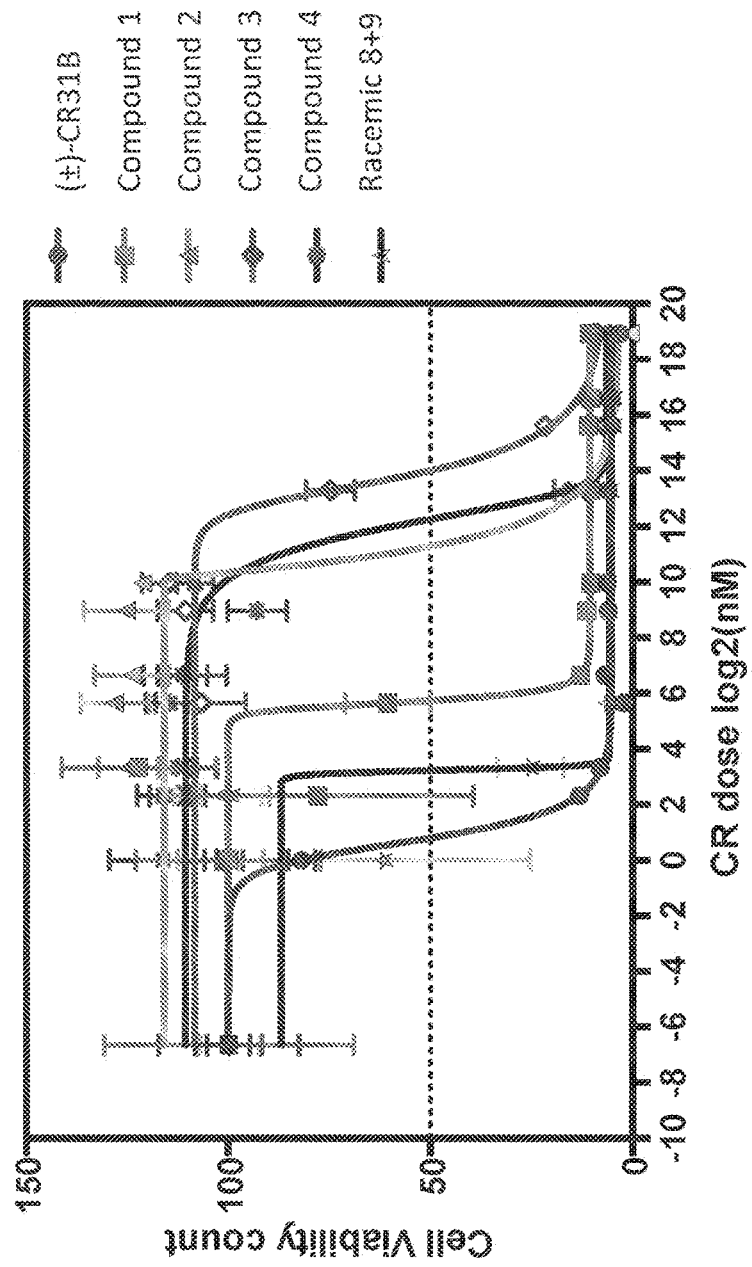
FIG. 3 shows the effect of compounds of the invention on viability of KOPTK1 T-ALL cells in vitro.

FIG. 3 shows the cell viability assay results of various compounds of the invention on the KOPTK1 T-ALL cell line.

Example 6. Activity Against G-Quadruplex-Mediated Translation

Figure 4B:
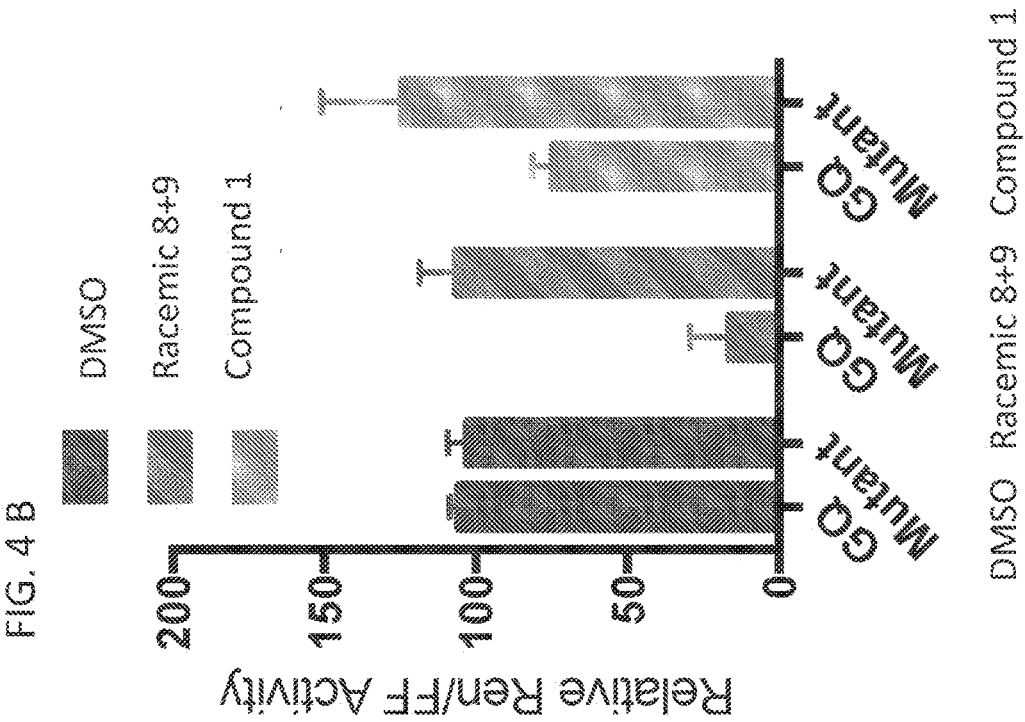
FIGS. 4A and 4B show the effect of compounds of the invention on G-quadruplex-mediated translation.
Figure 4A:
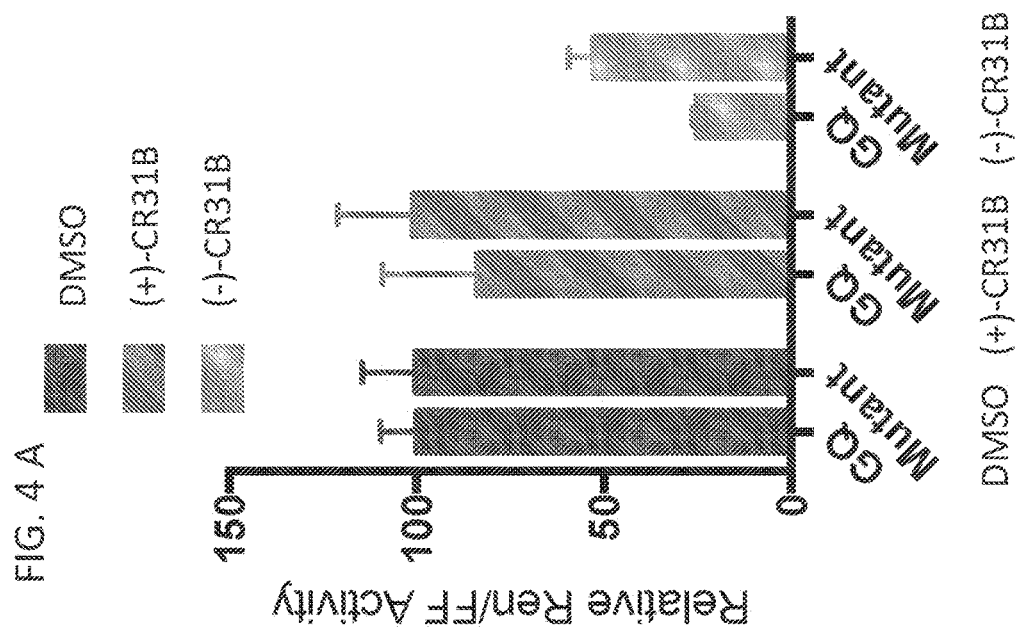

FIGS. 4A and 4B show the results of an assay for inhibition of G-quadruplex-mediated translation by compounds of the invention. Four tandem repeats of the $(CGG)_4$ 12-nucleotide motif (GQs) or random sequence matched for length and GC content (random) were cloned into the 5'UTR of *Renilla* luciferase plasmid pGL4.73. Empty Firefly luciferase plasmid pGL4.13 or HCV-IRES Firefly were used as internal controls. Luciferase assays were performed using Dual-Luciferase Reporter Assay System (Promega E1960) following the manufacturer's instructions.

GQ sequences were as follows (in bold):

(SEQ ID NO: 1)
CTAGGTTGAAAGTACTTTGACGGCGGCGGCGGTCAATCTTA

CGGCGGCGGCGGACATAGATACGGCGGCGGCGGTAGAAACT

ACGGCGGCGGCGGATTAGAATAGTAAA.

Random sequence matched for GC content:
(SEQ ID NO: 2)
CTAGGGCGCACGTACTTCGACAACGTCAGCGTTCAGCGTTC

CAACGTCAGCGTACAGCGATCCAACGTCAGCGTTCTGCGCT

ACAACGTCAGCGTATCCGCGTAGCACA.

Example 7. Biological Activity of Inventive Compounds In Vivo

Figure 5:
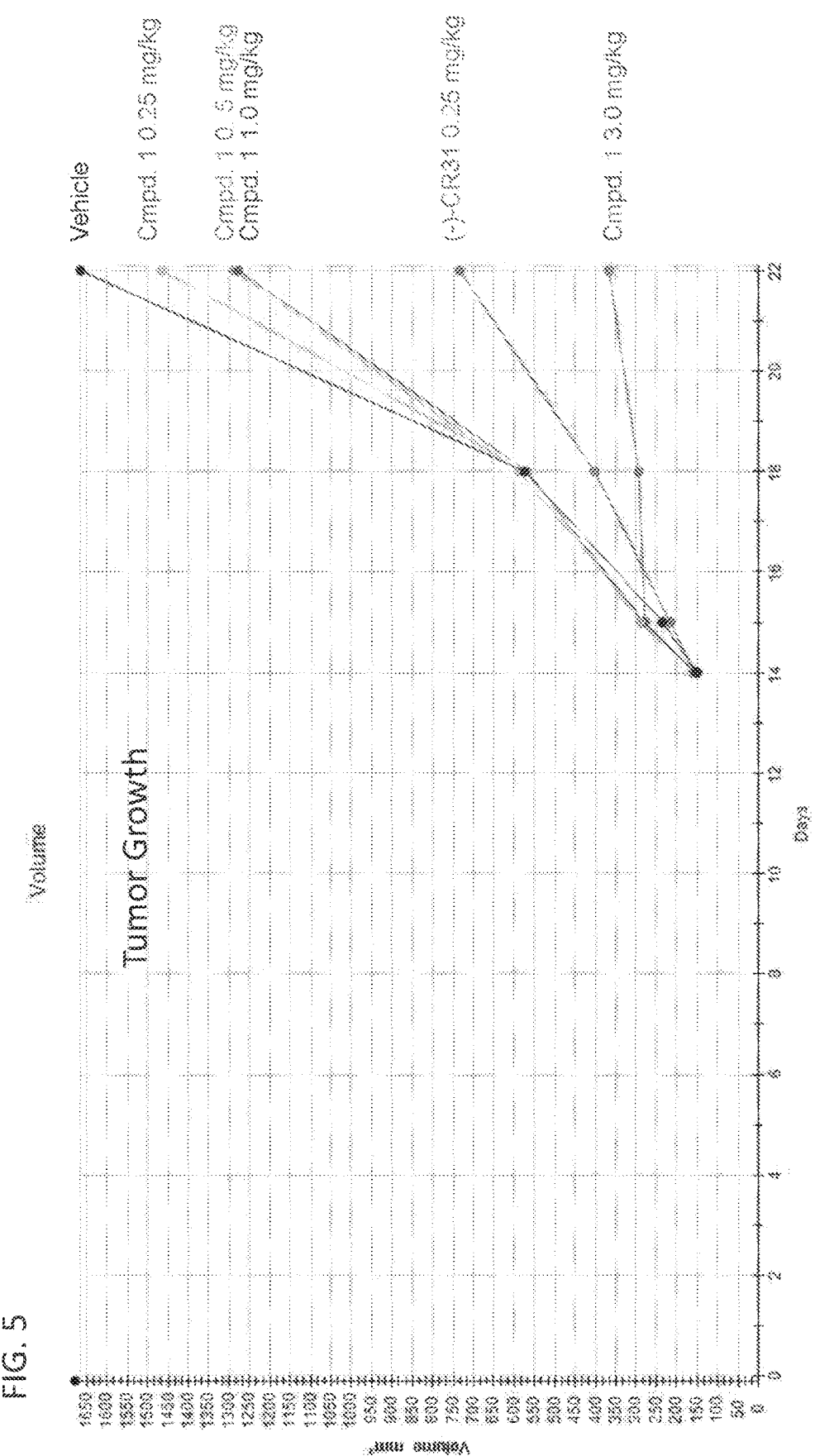
FIG. 5 shows the effect of a compound of the invention on tumor growth derived from KOPTK1 T-ALL cell line xenografts in vivo.
Figure 6:
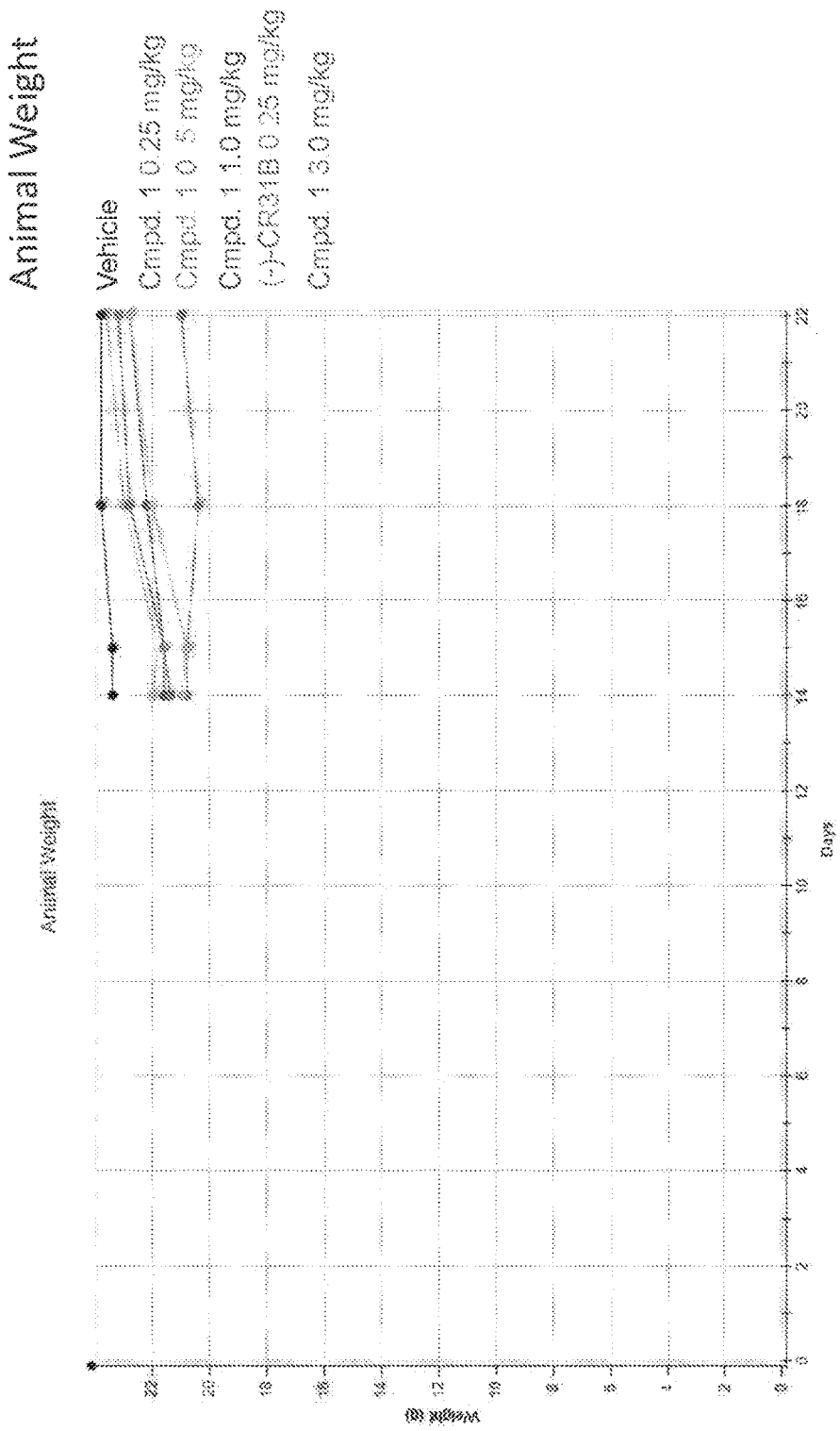
FIG. 6 shows the effect of a compound of the invention on animal weight following KOPTK1 T-ALL cell line derived tumors in a xenograft model.

FIG. 5 shows the tumor growth by volume, and FIG. 6 shows the body weights of tumor bearing animals that received a compound of the invention. Female NSGs mice, 6-8 weeks old, were injected with KOPT-K1, 5 million cells/mouse s.c. single flank with matrigel, then administered (−)-CR-31-B, 0.25 mg/kg i.v. Monday, Wednesday and Friday for 2 weeks, or Compound 1, 0.25, 0.5, 1.0 or 3.0 mg/kg i.v. following the same dosing regimen. The vehicle was 10% captisol. Drug treatment (n=5/group) was started when tumors reached ~100 mm3.

Mouse weight (FIG. 6) and tumor volumes (FIG. 5) were measured twice/wk.

Various modifications of the invention, in addition to those described herein, will be apparent to those skilled in the art from the foregoing description. Such modifications are also intended to fall within the scope of the appended claims. Each reference, including all patents, patent applications, and journal literature, cited in the present application is incorporated herein by reference in its entirety.

What is claimed is:

1. A compound represented by formula (I)

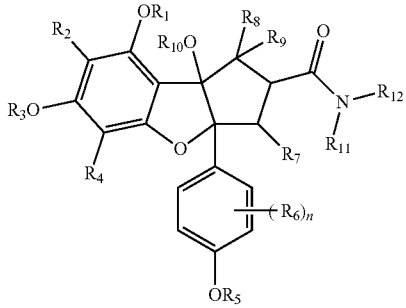

wherein
- $R_1$, $R_3$, and $R_5$ are each independently H, alkyl, —P(O)(OH)(OH), —$CH_2$—P(O)(OH)(OH), —P(O)(OH)(O-alkyl), —$CH_2$—P(O)(OH)(O-alkyl), —P(O)(O-alkyl)(O-alkyl), —$CH_2$—P(O)(O-alkyl)(O-alkyl), or (CO)-alkyl, or a pharmaceutically acceptable salt of —P(O)(OH)(OH), —$CH_2$—P(O)(OH)(OH), —P(O)(OH)(O-alkyl), or —$CH_2$—P(O)(OH)(O-alkyl), and
- wherein at least one of $R_1$, $R_3$, and $R_5$ is H, —P(O)(OH)(OH), —$CH_2$—P(O)(OH)(OH), —P(O)(OH)(O-alkyl), —$CH_2$—P(O)(OH)(O-alkyl), —P(O)(O-alkyl)(O-alkyl), —$CH_2$—P(O)(O-alkyl)(O-alkyl), or a pharmaceutically acceptable salt of —P(O)(OH)(OH), —$CH_2$—P(O)(OH)(OH), —P(O)(OH)(O-alkyl), or —$CH_2$—P(O)(OH)(O-alkyl);
- $R_2$ and $R_4$ are each independently H, alkyl, halo, nitro, OH, O-alkyl, SH, S-alkyl, CN, haloalkyl, O-haloalkyl, $NR_aR_b$, (CO)-alkyl, (CO)OH, (CO)O-alkyl, $SO_2NR_aR_b$, (CO)$NR_aR_b$, NH(CO)-alkyl, cycloalkyl, heterocycloalkyl, aryl, or heteroaryl, wherein aryl and heteroaryl are optionally substituted with alkyl, halo, nitro, OH, O-alkyl, SH, S-alkyl, CN, haloalkyl, O-haloalkyl, and $NR_aR_b$;
- $R_6$ is alkyl, halo, nitro, OH, O-alkyl, SH, S-alkyl, CN, haloalkyl, O-haloalkyl, $NR_aR_b$, (CO)-alkyl, (CO)OH, (CO)O-alkyl, $SO_2NR_aR_b$, (CO)$NR_aR_b$, NH(CO)-alkyl, cycloalkyl, heterocycloalkyl, aryl, or heteroaryl, wherein aryl and heteroaryl are optionally substituted with alkyl, halo, nitro, OH, O-alkyl, SH, S-alkyl, CN, haloalkyl, O-haloalkyl, and $NR_aR_b$;
- $R_7$ is aryl or heteroaryl, wherein aryl and heteroaryl are optionally substituted with alkyl, halo, nitro, OH, O-alkyl, SH, S-alkyl, CN, haloalkyl, O-haloalkyl, and $NR_aR_b$;
- $R_8$ and $R_9$ are each independently H, OH, alkyl, halo, O-alkyl, SH, S-alkyl, CN, haloalkyl, O-haloalkyl, $NR_aR_b$, (CO)OH, (CO)O-alkyl, $SO_2NR_aR_b$, (CO)N$R_aR_b$, or NH(CO)-alkyl;
- $R_{10}$ is H, alkyl, (CO)-alkyl, or (CO)$NR_aR_b$;
- $R_{11}$ and $R_{12}$ are each independently H, OH, alkyloxy, cycloalkyloxy, heterocycloalkyloxy, cycloalkylalkyloxy, heterocycloalkylalkyloxy, arylalkyloxy, heteroarylalkyloxy, aryloxy, or heteroaryloxy;
- $R_a$ and $R_b$ are each H or alkyl, or $R_a$ and $R_b$, together with the nitrogen atom they are attached, form a heterocycloalkyl group; and
- n is an integer from 0 to 4, or a pharmaceutically acceptable salt thereof.

2. The compound of claim 1, wherein $R_{11}$ is H.

3. The compound of claim 2, wherein $R_{11}$ and $R_{12}$ both are H.

4. The compound of claim 2, wherein $R_{11}$ is H and $R_{12}$ is alkyloxy or cycloalkyloxy.

5. The compound of claim 2, wherein $R_{11}$ is H and $R_{12}$ is OMe.

6. The compound of claim 1, wherein $R_3$ is H, —P(O)(OH)(OH), —$CH_2$—P(O)(OH)(OH), —P(O)(OH)(O-alkyl), —$CH_2$—P(O)(OH)(O-alkyl), —P(O)(O-alkyl)(O-alkyl), —$CH_2$—P(O)(O-alkyl)(O-alkyl), or a pharmaceutically acceptable salt of —P(O)(OH)(OH), —$CH_2$—P(O)(OH)(OH), —P(O)(OH)(O-alkyl), or —$CH_2$—P(O)(OH)(O-alkyl).

7. The compound of claim 1, wherein $R_3$ is H.

8. The compound of claim 1, wherein $R_5$ is H, —P(O)(OH)(OH), —$CH_2$—P(O)(OH)(OH), —P(O)(OH)(O-alkyl), —$CH_2$—P(O)(OH)(O-alkyl), —P(O)(O-alkyl)(O-alkyl), —$CH_2$—P(O)(O-alkyl)(O-alkyl), or a pharmaceutically acceptable salt of —P(O)(OH)(OH), —$CH_2$—P(O)(OH)(OH), —P(O)(OH)(O-alkyl), or —$CH_2$—P(O)(OH)(O-alkyl).

9. The compound of claim 1, wherein $R_5$ is H.

10. The compound of claim 1, wherein $R_5$ is —P(O)(OH)(OH) or —$CH_2$—P(O)(OH)(OH), or a pharmaceutically acceptable salt thereof.

11. The compound of claim 1, wherein $R_1$ is H, —P(O)(OH)(OH), —$CH_2$—P(O)(OH)(OH), —P(O)(OH)(O-alkyl), —$CH_2$—P(O)(OH)(O-alkyl), —P(O)(O-alkyl)(O-alkyl), —$CH_2$—P(O)(O-alkyl)(O-alkyl), or a pharmaceutically acceptable salt of —P(O)(OH)(OH), —$CH_2$—P(O)(OH)(OH), —P(O)(OH)(O-alkyl), or —$CH_2$—P(O)(OH)(O-alkyl).

12. The compound of claim 1, wherein $R_1$ is H.

13. The compound of claim 1, wherein $R_1$ is alkyl.

14. The compound of claim 13, wherein $R_1$ is methyl.

15. The compound of claim 1, wherein $R_2$ and $R_4$ are H and n is 0.

16. The compound of claim 1, wherein $R_{10}$ is H.

17. The compound of claim 1, wherein $R_8$ is H and $R_9$ is OH.

18. The compound of claim 1, wherein said compound of formula (I) is represented by a compound of formula (II)

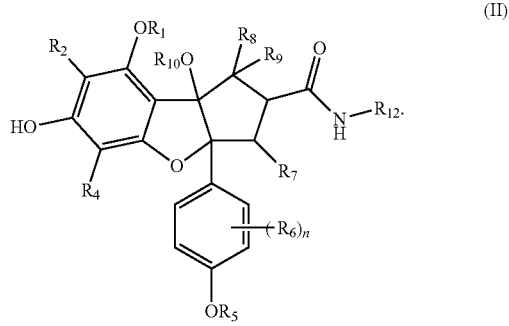

19. The compound of claim 18, wherein $R_{12}$ is H or OMe.

20. The compound of claim 1, wherein said compound of formula (I) is represented by a compound of formula (III)

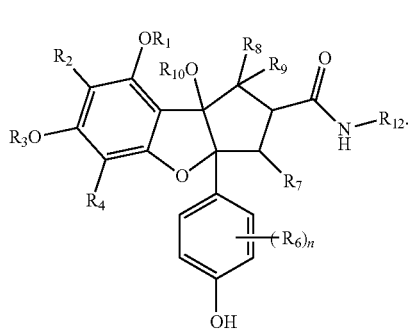

(III)

21. The compound of claim 20, wherein $R_{12}$ is OMe.

22. The compound of claim 20, wherein $R_{12}$ is H.

23. The compound of claim 1, wherein said compound of formula (I) is represented by a compound of formula (IV)

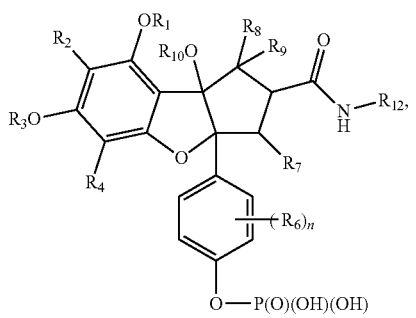

(IV)

or a pharmaceutically acceptable salt thereof.

24. The compound of claim 23, wherein $R_{12}$ is alkyloxy or cycloalkyloxy.

25. The compound of claim 23, wherein $R_{12}$ is OMe.

26. The compound of claim 1, wherein said compound of formula (I) is represented by a compound of formula (V)

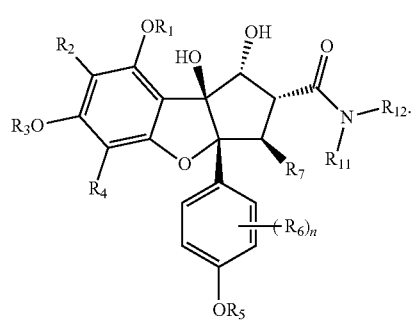

(V)

27. The compound of claim 1, wherein said compound of formula (I) is represented by a compound of formula (VI)

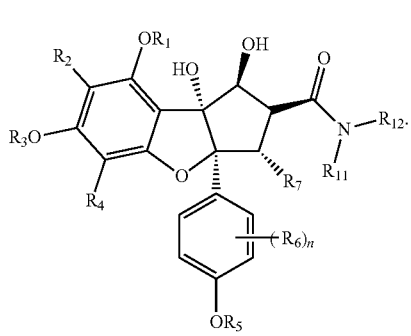

(VI)

28. The compound of claim 1, wherein said compound is

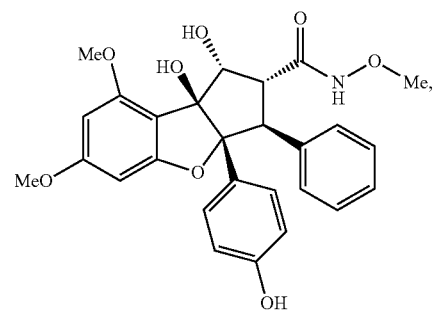

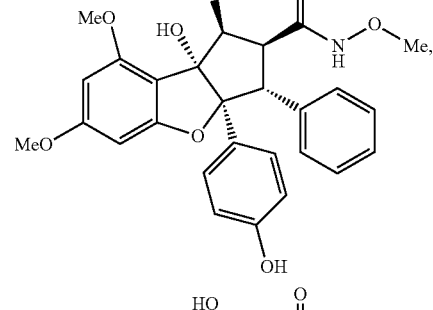

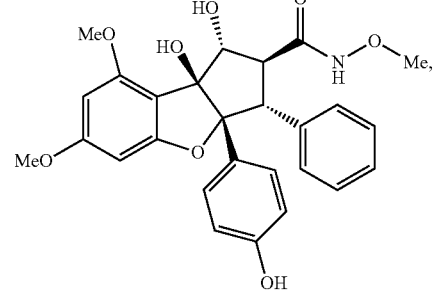

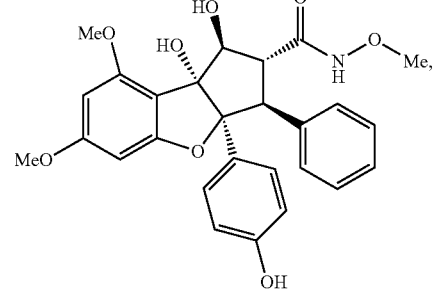

-continued

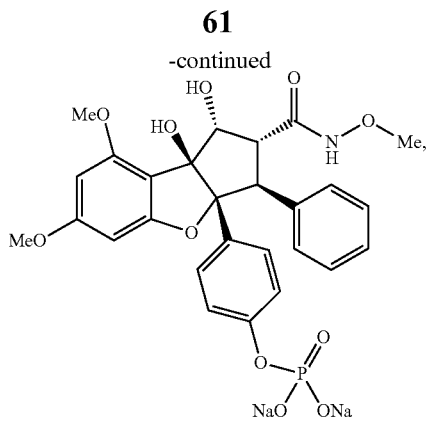

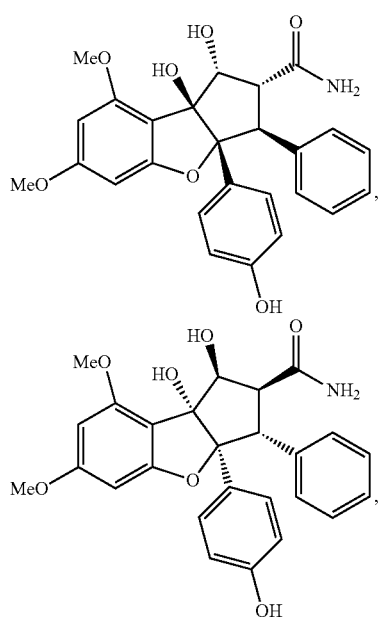

-continued

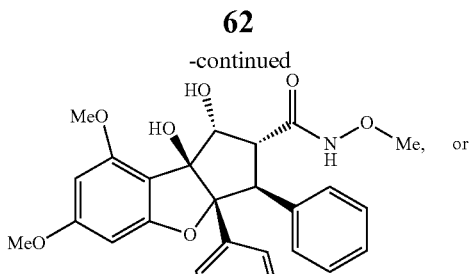

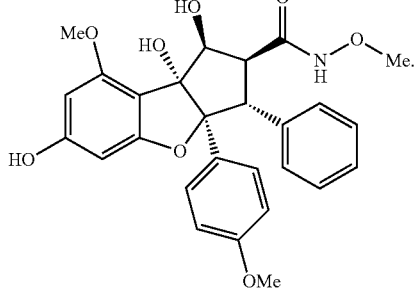

29. A pharmaceutical composition comprising a compound of claim 1 and a pharmaceutically-acceptable excipient, diluent or carrier.

30. A method for treating or intervening in the recurrence of a cancer or dysproliferative disease in a subject comprising administering to the subject a pharmaceutical composition of claim 29.

31. The method of claim 30 wherein the cancer is T-cell acute lymphoblastic leukemia, small cell lung cancer, renal cell carcinoma, squamous cell carcinoma of the head and neck, neuroblastoma, pancreatic cancer, transformed follicular lymphoma, mantel cell lymphoma, breast cancer, ovarian cancer, hepatocellular carcinoma, non-small cell lung cancer, gastric cancer, Ewing sarcoma or lung adenocarcinoma.

\* \* \* \* \*

SEQUENCE LISTING

<160> NUMBER OF SEQ ID NOS: 2

<210> SEQ ID NO 1
<211> LENGTH: 109
<212> TYPE: DNA
<213> ORGANISM: Artificial sequence
<220> FEATURE:
<223> OTHER INFORMATION: Synthetic

<400> SEQUENCE: 1
ctaggttgaa agtactttga cggcggcggc ggtcaatctt acggcggcgg cggacataga    60
tacggcggcg cggtagaaa ctacggcggc ggcggattag aatagtaaa               109

<210> SEQ ID NO 2
<211> LENGTH: 109
<212> TYPE: DNA
<213> ORGANISM: Artificial sequence
<220> FEATURE:
<223> OTHER INFORMATION: Synthetic

<400> SEQUENCE: 2
ctagggcgca cgtacttcga caacgtcagc gttcagcgtt ccaacgtcag cgtacagcga    60
tccaacgtca gcgttctgcg ctacaacgtc agcgtatccg cgtagcaca              109